United States Patent [19]
Duhamel et al.

[11] Patent Number: 5,817,890
[45] Date of Patent: Oct. 6, 1998

[54] PROCESS FOR PREPARATION OF HALOGENATED OR PSEUDOHALOGENATED CYCLIC ORGANIC COMPOUNDS

[75] Inventors: Lucette Duhamel; Pierre Duhamel, both of Mont Saint Aignan; Bertrand Leblond, Rouen; Jean-Marie Poirier, Darnetal, all of France

[73] Assignee: Rhone-Poulenc Chimie, Courbevoie Cedex, France

[21] Appl. No.: 401,254

[22] Filed: Mar. 9, 1995

Related U.S. Application Data

[62] Division of Ser. No. 139,049, Oct. 21, 1993, Pat. No. 5,424,460, which is a continuation of Ser. No. 869,297, Apr. 16, 1992, abandoned.

[30] Foreign Application Priority Data

Apr. 17, 1991 [FR] France ................................... 91 04700
Apr. 17, 1991 [FR] France ................................... 91 04701

[51] Int. Cl.$^6$ ................................................ C07C 39/26
[52] U.S. Cl. .......................... 568/772; 568/774; 568/775; 568/779
[58] Field of Search .................................... 568/775, 774, 568/779, 772

[56] References Cited

U.S. PATENT DOCUMENTS

| | | | |
|---|---|---|---|
| 3,236,874 | 2/1966 | Robinson et al. | 558/431 |
| 3,444,196 | 5/1969 | Schoot | 564/183 |
| 3,898,289 | 8/1975 | Schneider et al. | 568/772 |

FOREIGN PATENT DOCUMENTS

| | | |
|---|---|---|
| 1 186 846 | 2/1965 | Germany . |
| 1 221 622 | 7/1966 | Germany . |
| 1 243 184 | 6/1967 | Germany . |
| 1 022 203 | 9/1966 | United Kingdom . |
| 1 066 812 | 4/1967 | United Kingdom . |

OTHER PUBLICATIONS

Mandal et al., Synthesis, (1985), 3, pp. 274–275.

*Primary Examiner*—Johann Richter
*Assistant Examiner*—Laura L. Stockton
*Attorney, Agent, or Firm*—Finnegan, Henderson, Farabow, Garrett & Dunner, L.L.P.

[57] ABSTRACT

The present invention relates to new fluorinated hexane compounds corresponding to the following general formula (II):

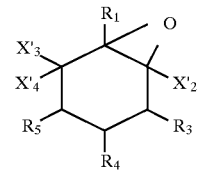

in which $X'_2$, $X'_3$, and $X'_4$ are the same or different, and denote a halogen or a pseudohalogen, preferably a halogen, more preferably chlorine and fluorine, with the condition that, when $R_1$ is hydroxyl, cyano, amido, imido, ethoxy, benzyloxy, cyclohexyloxy and tert-butoxy, not all the halogens can simultaneously be chlorine and $R_4$, $R_3$ and $R_5$ are simultaneously equal to H;

$R_1$ denotes a hydrogen, a hydrocarbon chain such as an alkyl chain, alkoxy, cycloalkyl ether, an aromatic group, aromatic ether or an alkoxy, carbonyl, carboxyl or acyloxy, cyano, amido, imido or hydroxyl group;

$R_4$ denotes a hydrogen, a fluorine atom, a hydrocarbon chain such as, for example, an alkyl chain, an aromatic group or a carbonyl, carboxyl or carboxamide group or else a radical joined to the hexane ring by a chalcogen or by an element of Group V, preferably of the first Period, such as an amido, alkoxy or acyloxy group;

in which the radicals $R_3$ and $R_5$, which are different or preferably the same, denote a fluorine, or preferably hydrogen, atom or also a hydrocarbon chain as defined above in the case of $R_4$.

11 Claims, 4 Drawing Sheets

PROCESS FOR PREPARATION OF HALOGENATED OR PSEUDOHALOGENATED CYCLIC ORGANIC COMPOUNDS

This is a division of application Ser. No. 08/139,049 filed Oct. 21, 1993 now U.S. Pat. No. 5,424,460, which is a continuation of application Ser. No. 07/869,297, filed Apr. 16, 1992 now abandoned.

BACKGROUND OF THE INVENTION

1. Technical Field

The present invention relates to new synthesis intermediates which now allow preparation of products which are reportedly difficult to prepare and especially to halogenated benzene derivatives.

The present invention relates more particularly to synthetic compounds derived from cyclohexanone and especially by substitution of the α positions using halogen or pseudohalogen atoms.

2. Prior Art

By way of example and to show the importance of the products of the present invention, halogenated derivatives make it possible to obtain 2,6-dihaloanilines which are intermediates that can be employed to obtain phenylacetic derivatives. These derivatives can have antiphlogistic, analgesic and antipyretic properties. Insofar as the conversion of 2,2,6,6-tetrahomohalocyclohexanones to useful products is concerned, reference may be made to the European Patent published under No. 0,313,740.

Published Japanese Patent Application No. 23,418/1967 describes the synthesis of the medications referred to above. Despite the importance of tetra(pseudo)halogenated cyclohexanones, synthesis processes which permit access to these products are either complicated or have never been described.

For example, the synthesis or isolation of the compound comprising 2,2,6,6-tetrafluorocyclohexanone has not, to the applicants' knowledge, been described in the literature.

It is therefore an object of the present invention to overcome these and other difficulties encountered in the prior art.

One of the objects of the present invention is to provide new reaction intermediates which make it possible to produce halogenated, especially dihalogenated, aromatic derivatives and especially halophenols.

Another object of the present invention is to provide cyclohexane derivatives with extremely diverse uses for obtaining various organic compounds.

Another object of the present invention is to provide synthetic processes making it possible to obtain the intermediate compounds specified above.

Another object of the present invention is to provide processes permitting the aromatization of the above products.

Additional objects and advantages of the instant invention will be set forth in part in the description which follows and in part will be apparent to a person with ordinary skill in the art from the description, or may be learned by practice of the invention. The objects and advantages of the invention may be realized and attained by means of the instrumentalities and combinations particularly pointed out in the appended claims.

SUMMARY OF THE INVENTION

These and other objects have been obtained according to the present invention which comprises novel cyclohexane epoxy derivatives and novel methods for their production.

The compounds according to the invention correspond to the following general formula (II):

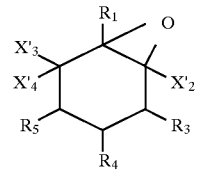

in which $X'_2$, $X'_3$ and $X'_4$ (which correspond on a one-to-one basis to $X_2$, $X_3$ and $X_4$ or $X_1$, $X_2$ and $X_3$ of formula I infra), are the same or different, and denote a halogen or a pseudohalogen, preferably a halogen, more preferably chlorine and/or fluorine; with the condition that, when $R_1$ is hydroxyl, cyano, amido, imido, ethoxy, benzyloxy, cyclohexyloxy and tert-butoxy, not all the halogens can simultaneously be chlorine;

$R_1$ also denotes a hydrogen, a hydrocarbon chain such as, for example,
an alkyl chain, an aromatic group, aromatic ether, cycloalkyl ether or an alkoxy, carbonyl, carboxyl or acyloxy or even hydroxyl group;

in which $R_4$ denotes a hydrogen, a fluorine atom, a hydrocarbon chain such as, for example, an alkyl chain, an aromatic group, or a carbonyl, carboxyl or carboxamide group or else a radical joined to the hexane ring by a chalcogen or by an element of Group V, preferably of the first Period, N, P, As, Sb, Bi, such as an amido, alkoxy or acyloxy group;

the radicals $R_3$ and $R_5$, which are different or preferably the same,
denote an atom of fluorine, or preferably hydrogen, or also hydrocarbon chains as defined above for $R_4$.

Pseudohalogens are intended to mean groups in which the anions form excellent leaving groups, more precisely they are intended to mean oxygenated acids whose Hammett constant demonstrates an acidity at least equal to that of formic acid, preferably of trifluoroacetic acid. Typical examples of the pseudohalogens are the sulfonyloxy groups originating from triflic acid, $CF_3SO_3$, or para-toluenesulfonic acid and highly acidic carboxylic acids such as alpha-halogenated, preferably alpha-fluorinated, acids.

The term alkyl is intended to be taken in the etymologically accepted meaning of "alcoyle" set forth in the *Larousse Dictionary* in three volumes (1970) and not defined very restrictively as, for example, by the IUPAC rules. Typical examples of this class are: alkyls (according to the definition in *Dictionary of Chemistry* by Clement Duval published by Presses Scientifiques Internationales), cycloalkyls, aralkyls which may be substituted or functionalized provided that substituents or functional groups are substantially inert to the reactants according to the present invention, for example, alkyls derived from polyethylene glycol hemiethers.

Although there is no strict limit, it is rare for the number of carbon atoms per substituent to exceed 15 and even 10 (i.e., up to 15 or up to 10 carbon atoms). The total number of the carbons of the substituents taken as a whole rarely exceeds 30, and in general 20 (i.e., up to 30 or up to 20 carbon atoms). Accordingly, these are the ranges of the carbon atoms per substituent.

In formula (II) above, the hydrogens are not shown and the numbering of the ring carbons corresponds to the indices of the radicals R.

One of the most interesting properties of the epoxides according to the present invention is that they always open towards the central carbon, that is to say the carbon numbered 1 in the present description which is surrounded by carbons substituted by halogens or pseudohalogens that carry the alcohol functional group after the epoxide is opened.

DETAILED DESCRIPTION

Figure 1:
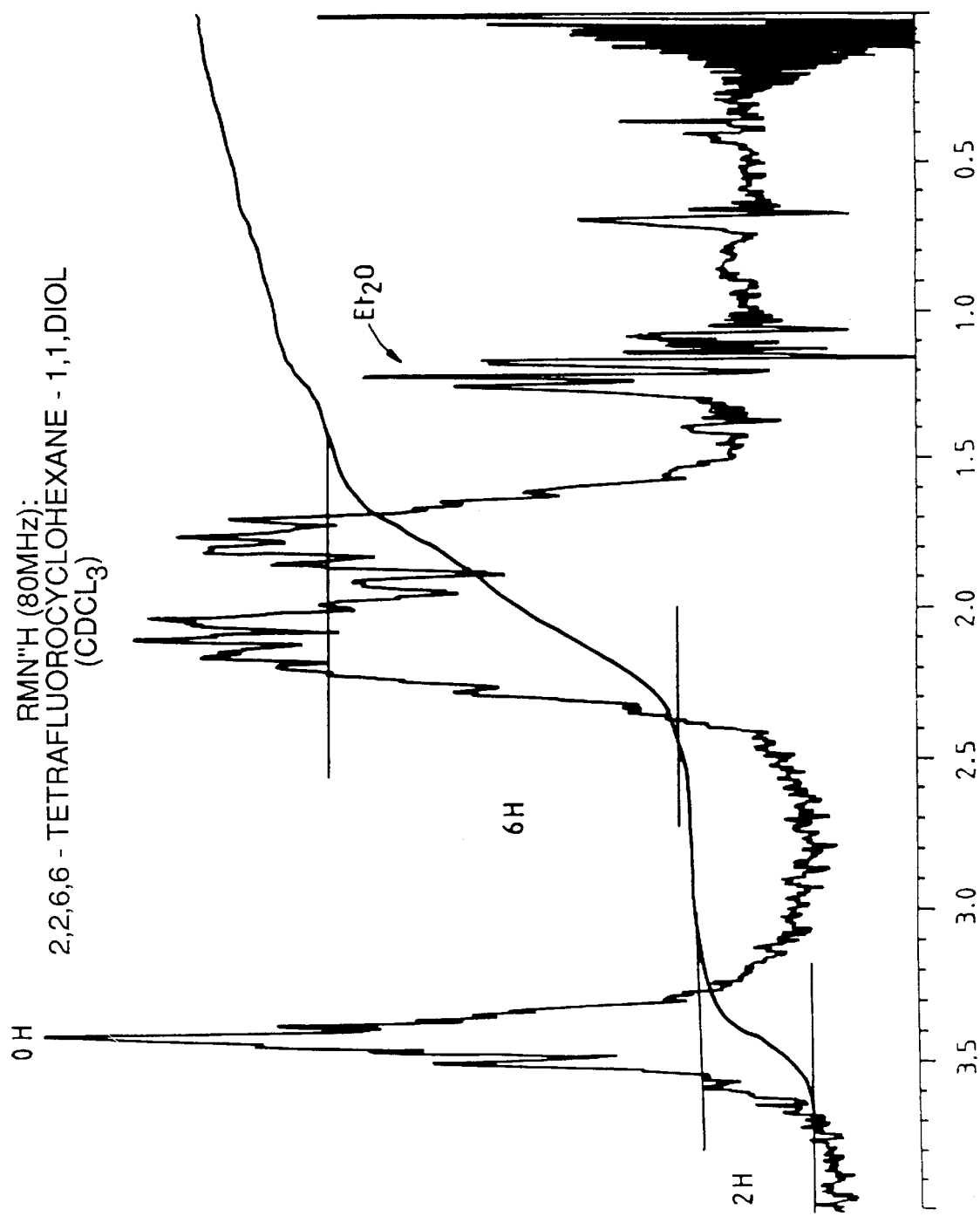
FIGS. 1 to 4 show the carbon 13 proton NMR spectrum and the mass spectrum of 2,2,6,6-tetrafluoro-1,1-cyclohexanediol obtained according to the present invention.
Figure 2:
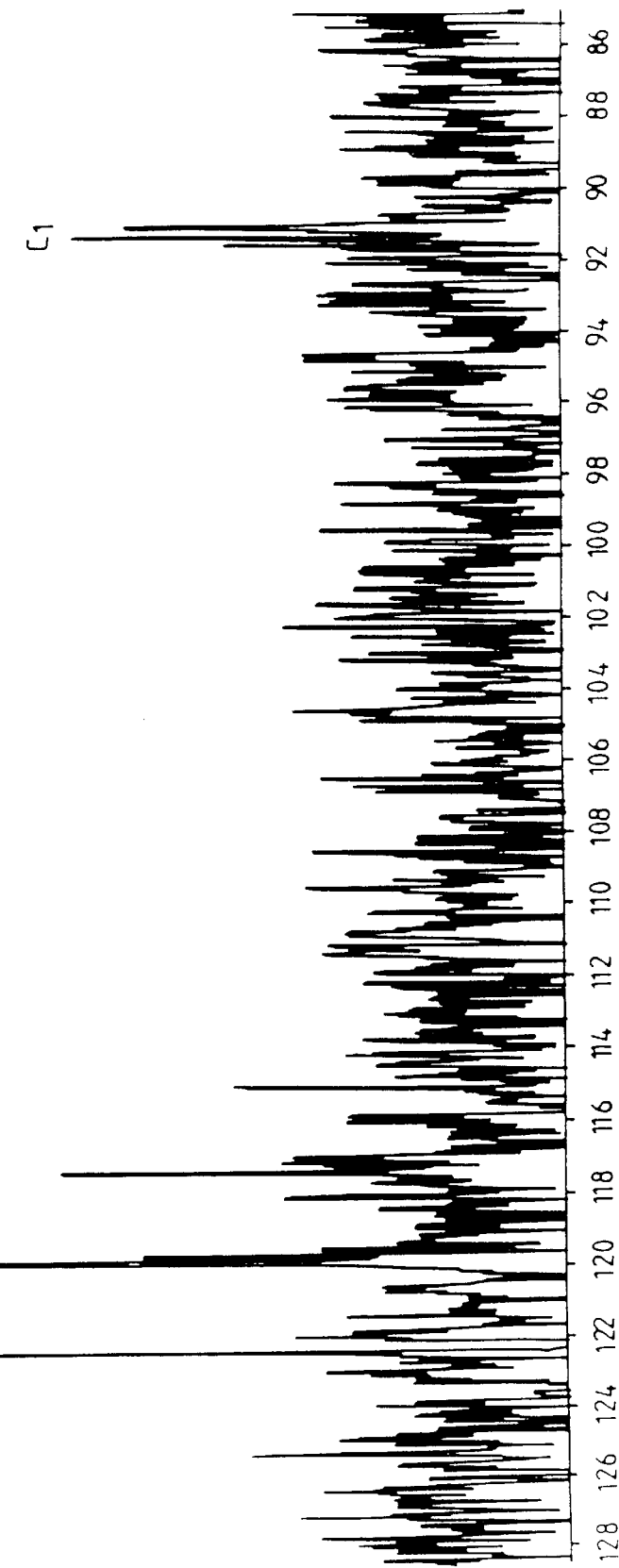
Figure 3:
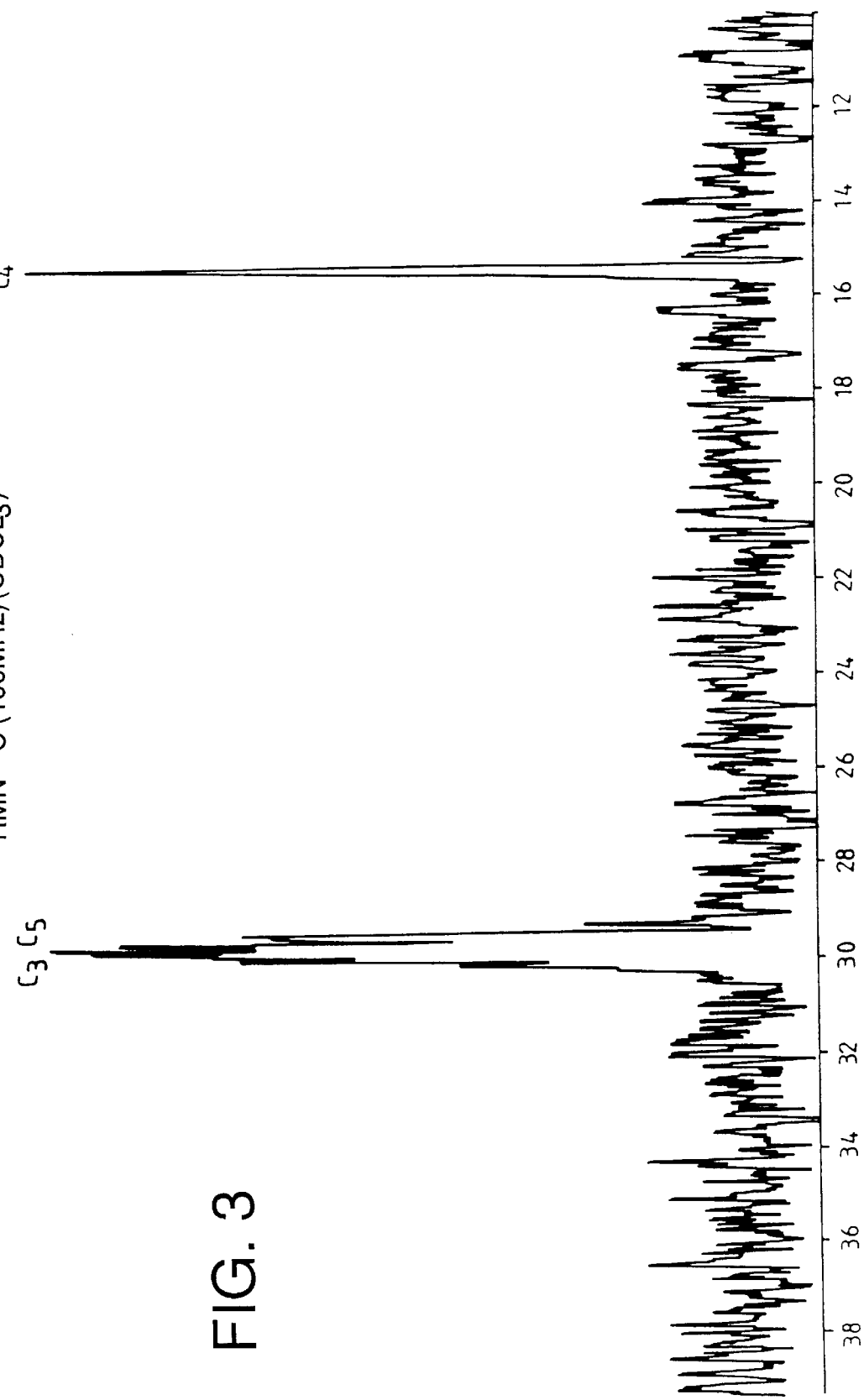
Figure 4:
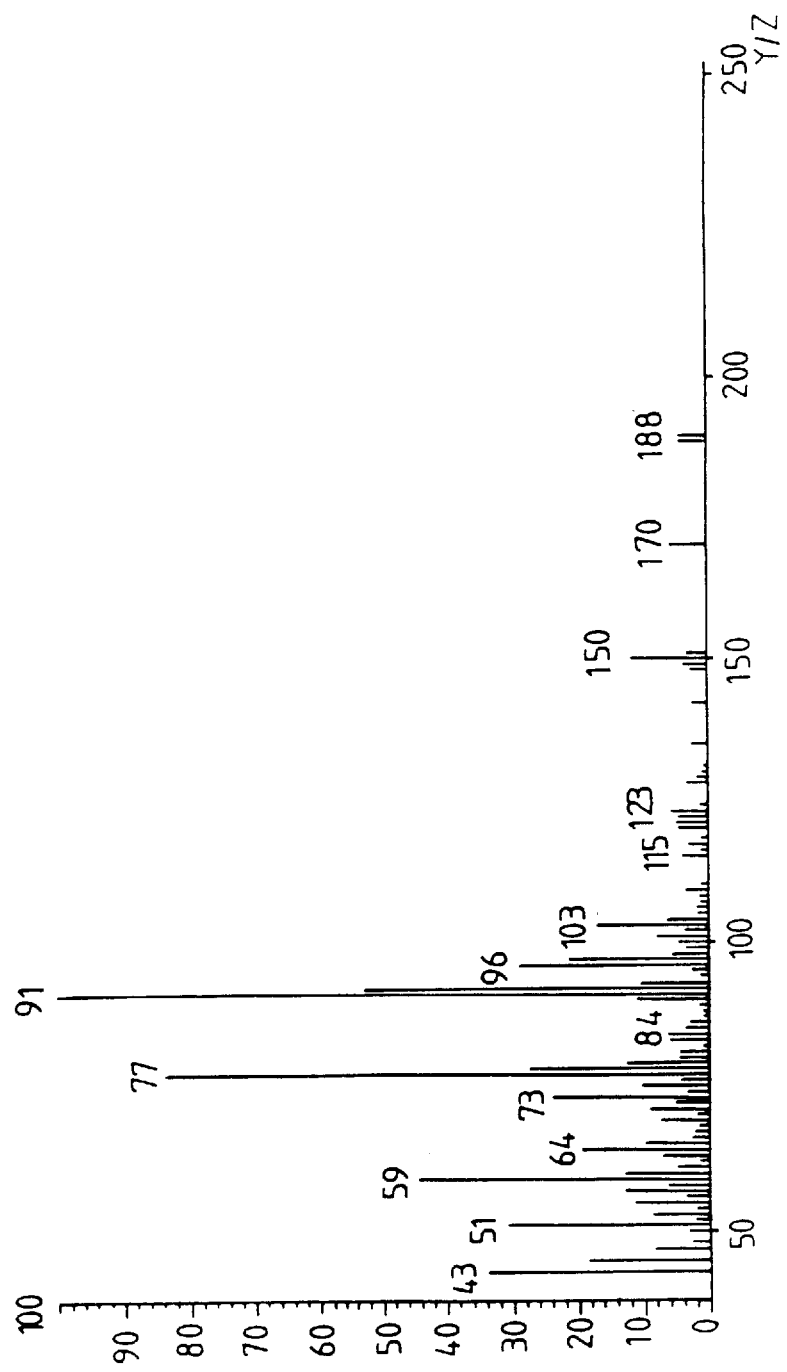

The above epoxides, the access routes to which are not described in the prior art, can very generally be prepared by the action of a base on an alcohol of general formula I or I' (infra).

The epoxide is generally made by the attack of the anion corresponding to the alcohol on a carbon adjoining that which carries the alcohol. The choice of the leaving group, as regards its nature and its position, is determined as follows:

the leaving group is in a trans position relative to the hydroxyl functional group;

when two leaving groups are possible, it is the more active leaving group which will be very preferentially ejected;

when the two possible leaving groups are the same, that situated on the same carbon as the most electronegative halogen will be the one which will be very preferentially ejected.

The epoxides can be prepared from alcohols carrying a hydrogen as well as a (hydro)carbon chain on the same carbon as the alcohol functional group.

The epicyclization reaction, sometimes referred to hereinafter by the term of epoxidation, advantageously takes place under the following conditions:

in a polar phase, which is preferably aqueous, or hydroorganic if the solubility of the derivative of formula I or I' makes it desirable; it is highly preferable that the said polar phase should be capable of dissolving, at least partially, the base and the alcohol I or I' at the same time; advantageously the solubility of the alcoholic substrate is at least equal to $10^{-3}M$, more preferably to $10^{-2}M$, and that of the base to $10^{-3}N$, more preferably to $10^{-2}N$;

at a temperature between the initial melting point of the reaction mixture and 100° C., preferably between 0° C. and 50° C., in general between 0° C. and ambient temperature (approximately 20° C.);

employing a strong base whose associated pKa is at least equal to 10, preferably to 12, more preferably a very strong base (such as an alkali metal hydroxide or a tetraalkylammonium hydroxide) in a quantity at least equal to the stoichiometric quantity (unless the reaction is only to be partially carried out), and preferably an excess is used;

when a rapid reaction is desired the concentration of soluble base in excess relative to the stoichiometric quantity is advantageously at least decinormal, preferably at least normal;

the base is added progressively, especially to make temperature control easier;

since the epoxide is more lipophilic than the halohydrin, it is possible to reduce the likelihood of potential side reaction(s) by carrying out the reaction in a two-phase medium throughout or during a part of the reaction; substantially inert solvents are then employed which are good solvents for cyclohexane epoxides and which are not miscible in all proportions with the aqueous phase, such as, for example, ethers, esters, organohalogen compounds or mixtures thereof.

The compounds of formula I are

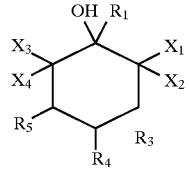

in which $X_1$, $X_2$, $X_3$, and $X_4$, may be the same or different, and denote a halogen or a pseudohalogen;

$R_1$ denotes hydrogen, cyano, amido, a hydrocarbon group, an aromatic group or an alkoxy, carbonyl, carboxyl or acyloxy or hydroxyl group;

$R_4$ denotes a hydrogen, a fluorine atom or a hydrocarbon chain;

$R_3$ and $R_5$ may be the same or different and denote fluorine, or hydrogen or a hydrocarbon group;

with the additional condition that, when $R_1$ is hydroxyl, not all the halogens can simultaneously be chlorine or bromine and, when $R_1$ is hydrogen, cyano or amido, not all the halogens can simultaneously be chlorine.

The cyclohexane alcohols which are direct or indirect precursors of the epoxides according to the present invention have the formula (I'), where the hydrogens are not shown, below:

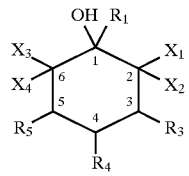

$X_1$, $X_2$, $X_3$ and $X_4$, are the same or different, and denote a halogen or a pseudohalogen, preferably a halogen, more preferably chlorine and fluorine;

$R_1$ denotes a hydrogen, a hydrocarbon chain such as, for example, an alkyl chain, an aromatic group, or an alkoxy, carbonyl, carboxyl, acyloxy or hydroxyl group;

$R_4$ denotes a hydrogen, a fluorine atom, a hydrocarbon chain such as, for example, an alkyl chain, an aromatic group, or an alkoxy or acyloxy group;

$R_3$ and $R_5$, which are different or preferably the same, denote an atom of fluorine, or preferably hydrogen, or hydrocarbon chains as defined above for $R_4$; or have the formula (I) resembling the formula (I') but with the additional condition that, when $R_1$ is hydroxyl, not all the halogens can simultaneously be chlorine or bromine and, when $R_1$ is hydrogen, cyano or amido, not all the halogens can simultaneously be chlorine.

Products equivalent to the 1,1-diols, such as 1-ketones are also produced by the present invention. Depending on the case, the compounds of formula I or I' above, which are other than 1,1-diols or equivalent (ketones) can be obtained, respectively, by reduction of the corresponding ketones (in general in hydrate form), by the action of organometallic compounds, or by opening of the epoxides. In the case of the 1,1-diols or equivalents these compounds can be prepared by oxidation of the corresponding alcohols.

In general, the first alcohol is an alcohol obtained by reduction of a tetrahomohalogenated derivative of an existing cyclohexanone. The reaction which is best known is that obtained by reduction of 2,2,6,6-tetrachlorocyclohexanone. This reaction is described in the following papers:

Tanaka, Kawazoe, Taguchi, *Yakuqaku Zasshi* (Japan) 1975, 95, 238, employing an alkali metal formate/formic acid mixture at 160°–170° C.; M. Jamshaid, M. Alam, *J. Pharm.* (Lahore) 1983 4(1–2), 101–3; Chem. Abs. 102; 166348u, employing lithium aluminum hydride or sodium borohydride.

However, according to the present invention, it has been shown that lithium aluminum hydride can be employed in the presence of ethers; it is also possible to employ isopropylmagnesium chloride at –20° C.

One of the best ways of preparing these tetrahalo alcohols by reduction is to employ borohydrides, advantageously those of alkali metals, generally sodium for reasons of economy, in the presence of a mixture of an ether, advantageously diethyl ether, and an alcohol, preferably methyl alcohol, at room temperature, that is to say at a temperature of between 0° and 50° C., preferably between 15° and 30° C.

The preferred ratio of the ether to the alcohol, by volume, is advantageously between 10 and 1, preferably in the neighborhood of 10 (in the present description, and as is conventional, the position zeros are not considered to be significant digits, i.e. 10 is a rounded number).

Above all, these alcohols can also be obtained by opening of the corresponding epoxides (and, as is the subject of the present invention) by means of a halide or pseudohalide ion, rendered nucleophilic.

The epoxide opening reaction takes place according to rules which have been determined during the study which has led to the present invention.

These rules can be summarized as follows:

The reaction takes place as if the mechanism in question was not a nucleophilic substitution of the second order (SN2), that is to say without inversion of configuration. In other words, after reaction, the halogen or pseudohalogen is situated in a cis configuration in relation to the alcohol originating from the oxygen bridge, thus, everything happens as if the bond between the carbon in the position adjoining carbon 1 (that is to say one of the carbons 2 or 6) and the oxygen did not move, but, as if, instead of joining the carbon to the oxygen of the oxirane, it joined the carbon to a halogen or to a pseudohalogen.

It is thus possible to make a halohydrin with any halogen or pseudohalogen by employing the techniques according to the present invention. Nevertheless, there are differences: the halogens considered as a leaving group can be classified in the order of the increasing atomic numbers of the halogens: the higher their rank, the better they are. Conversely, the lighter they are, the better is their nucleophilicity.

More specifically, according to the present invention, these epoxides are opened by Bronsted or Lewis acids comprising the halide or the pseudohalide in its molecule.

The preferred Lewis acids are either those which correspond to the trihalides of the elements of column III B of the Periodic Classification of the elements (defined by the French Chemical Society in the supplement to Bull. Soc. Chim. Fr. No. 1, January 1966), or those capable of existing in the form of various etherates (the latter may originate from symmetric or unsymmetric, cyclic or noncyclic ethers), or those having the two properties.

The preferred Bronsted acids are those in which the halide or pseudohalide ion constitutes the associated base, advantageously in order to facilitate their handling in the presence of a tertiary amine advantageously of low basicity, preferably amines considered to be tertiary and which contain, as base source, a nitrogen atom inserted into an aromatic ring, such as, for example, optionally substituted pyridines, e.g., picolines or quinolines.

Since the Bronsted acid is simpler to use, it is generally preferred. However, Lewis acids in principle give reactions which are more selective.

Although the operating conditions depend on the quantities and specificities of the reactants and of the substrates, it is possible to indicate, more by way of general directions than by way of strict rules, the operating conditions which are considered, independently of each other, to be preferred and are set out as follows.

The temperature is advantageously between the initial melting point and 100° C., preferably between 0° C. and 50° C., most commonly in the neighborhood of room temperature (approximately 20° C.). When a Lewis acid is employed, especially in the case of $BF_3$, the temperatures to be taken into account are higher, the preferred region is then in the neighborhood of 100° C. It is preferred to start the reaction at low temperature, that is to say in the bottom region of the ranges specified above, and then to allow the temperature to rise slowly to the desired temperature, generally room temperature.

The pressure is of little importance; for reasons of simplicity atmospheric pressure is generally employed. However, if it is desired to control a temperature by a reflux, it is easily possible to work at reduced pressure or at a pressure above atmospheric pressure.

Use is preferably made of solvents which are sufficiently polar to dissolve the epoxides well, together with the alcohols obtained by this technique. Among the preferred solvents there should be mentioned halogenated, generally chlorinated, solvents, such as methylene chloride, dichloroethanes, especially 1,2-dichloroethane, or trichloroethylene. If it is desired to purify the reaction mixture to remove the undesired byproducts of the reaction, conventional separating techniques can be employed such as, for example, flash chromatography on silica.

Insofar as unspecified parameters are concerned, these are known to a person skilled in the art and reference can be made to the examples to determine the optimum use regions of the parameters.

This selectivity of attack, this remarkable stereoselectivity, thus makes it possible to change all the halogens progressively by a succession of formation and of opening of epoxides.

In order to explain the mechanisms better, equations 1 to 19 herein give reaction schemes showing the part played by the geometry of the molecules in the progressive replacement of the halogens or pseudohalogens.

These successions of opening and closing of epoxide allow the substitutions of the halogens to be well-controlled in a highly selective manner in relation to each other. This is perfectly exemplified by the inversion of the configuration shown in the equations 14 to 18. Here the problem is to make a difluoro compound containing a fluorine in position 2 and a fluorine in position 6. This arrangement makes it possible to facilitate the aromatization to give one of the optionally substituted difluorobenzenes in better yields than the trifluoro compound.

EQUATION 1

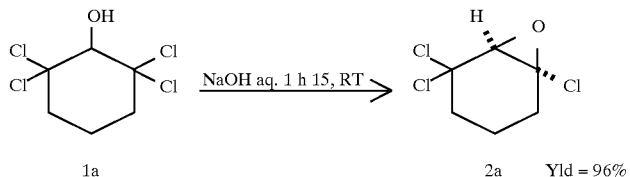

EQUATION 2

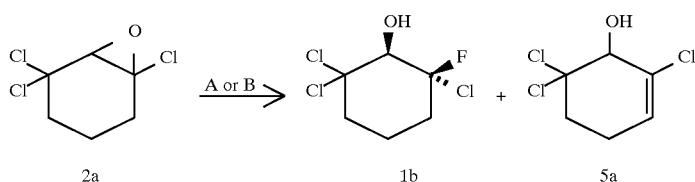

ROUTE A: HF/pyridine; 3 h 30; −35° C. then RT  1b/5a = 85/15  Yld = 99%  *Yld = 82% as pure 1b
ROUTE B: 0,53 eq. BF$_3$, Et$_2$O; 3 h  1b/5a = 100/0  Yld = 92%  after "flash"
1,2-dichloroethane at reflux.  *chemical purification

EQUATION 3

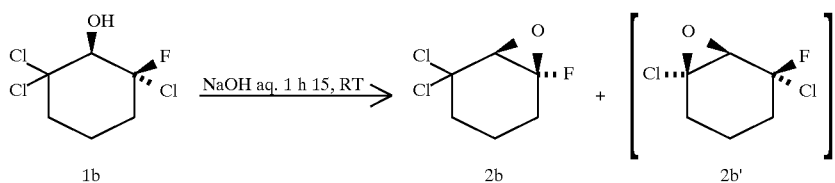

Proportion 2b/2b' = 93/7   Yld = 96%

EQUATION 4

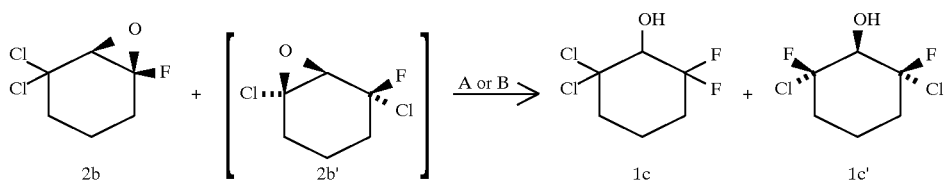

| | Reaction conditions | Proportion | Overall yield |
|---|---|---|---|
| A) HF/pyridine | 1 h 20; 0° C. then RT | 1c/1c' = 93/7 | 86% |
| B) BF$_3$, Et$_2$O | 1 h 45; dichloroethane at reflux | 1c/1c' = 93/7 | 82%* |
| | *1c is purified by "flashchromatography" | | |

EQUATION 5

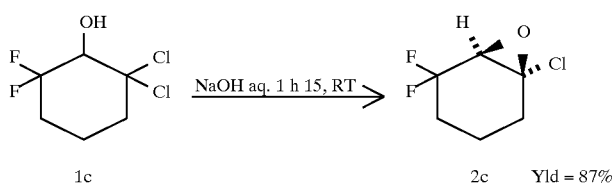

EQUATION 6
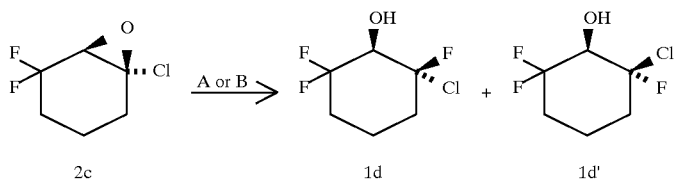
| Reactants | Reaction conditions | Proportion 1d/1d' | Overall yld |
|---|---|---|---|
| A) HF/pyridine | 2 h; 0° C. then RT | 83/17 | 82.5% |
| B) BF$_3$.Et$_2$O | 0,55 eq; 1 h 30; C$_2$H$_4$Cl$_2$ at reflux | 100/0 | 83.5% |
EQUATION 7
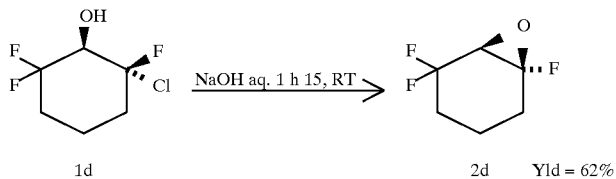
EQUATION 8
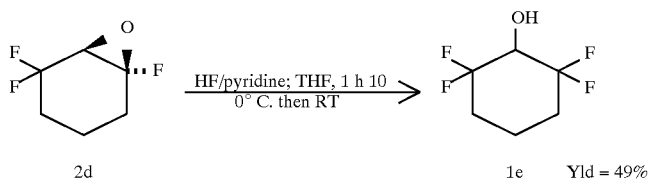
EQUATION 9
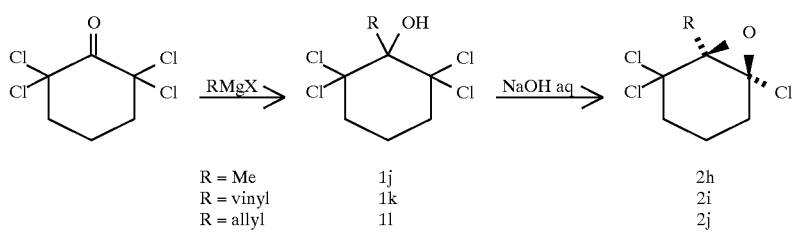
| R = Me | 1j | 2h |
| R = vinyl | 1k | 2i |
| R = allyl | 1l | 2j |
EQUATION 10
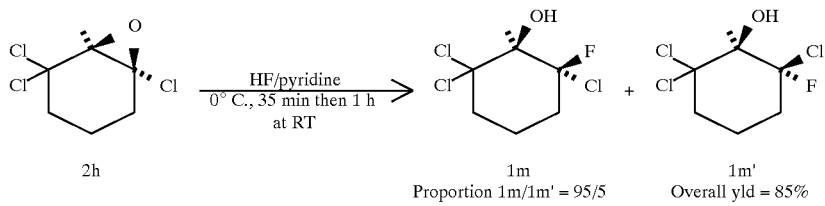
EQUATION 11
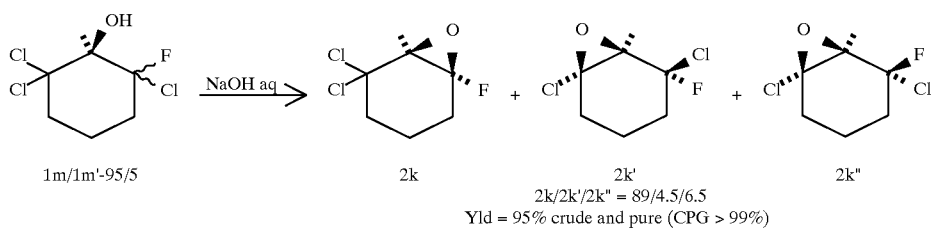

EQUATION 12
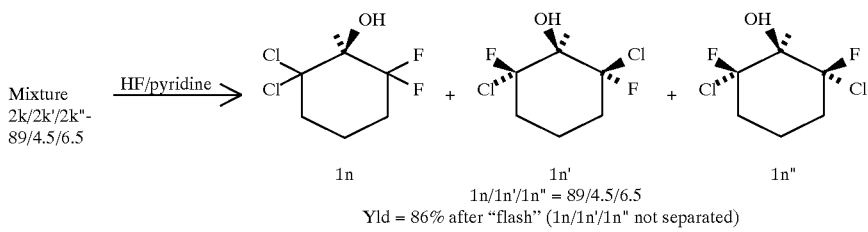
EQUATION 13
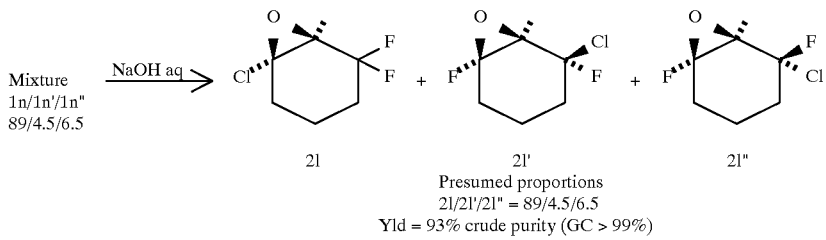
EQUATION 14–17
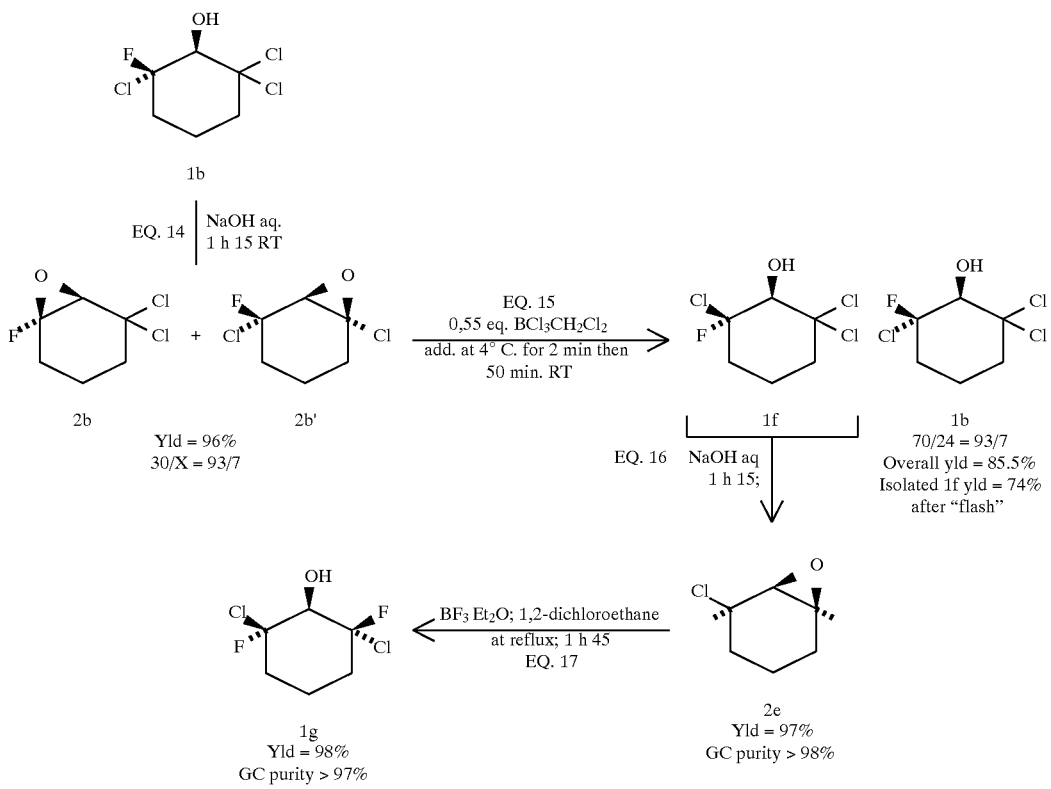

EQUATION 18

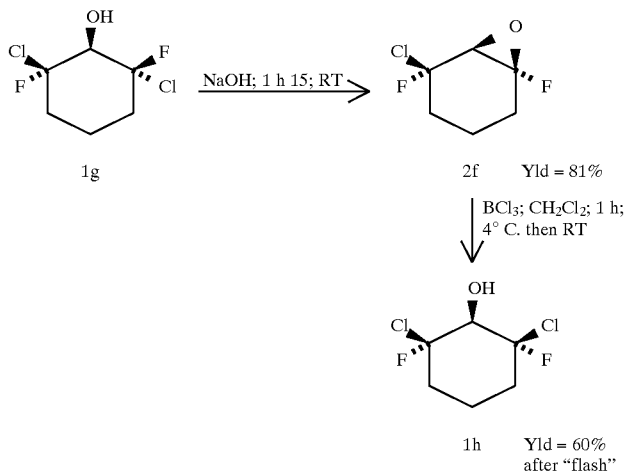

EQUATION 19

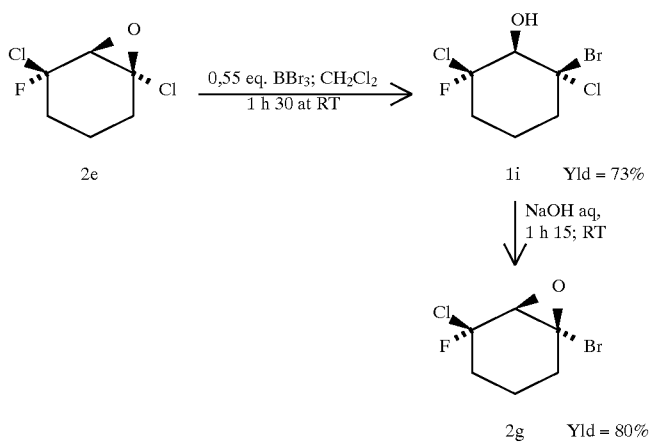

Discussion of Equations 1 to 19

In equations 1 to 19, the following numbering is employed:
alcohol 1a–1n
epoxides: 2a–2l
hydrates: 3a–3e
aromatics: 4a–4i
allyl alcohols: 5a–5b
trihalogenated ketones: 6a–6b Equations 1 to 8

Equations 1, 3, 5 and 7 show the reaction of the tetrahalocyclohexanols 1a, 1b, 1c and 1d to form the corresponding trihaloepoxides 2a, 2b, 2c and 2d in the presence of sodium hydroxide. The stereoselectivity is total for the equations 5 and 7 and partial in the case of equation 3 (the α-fluoro epoxide 2b is obtained with its α-chloro stereoisomer 2b' in the ratio 2b/2b'=13/1).

The equations 2, 4, 6 and 8 show the opening of the trihaloepoxides 2a, 2b, 2c and 2d by the HF/pyridine and/or $BF_3.Et_2O$ reactants to result selectively in the introduction of a fluorine atom in the cis position relative to the hydroxyl functional group. With the $BF_3.Et_2O$ reactant, the diastereoselectivity of the reaction is total for all the equations. With the HF/pyridine reactant this diastereoselectivity is still total in the case of the equations 2, 4 and 8 and 5/1 (cis 1d/trans 1d') in the case of equation 6.

Equations 9 to 13

Equation 9 shows an equation similar to equation 1, in which the starting point is 2,2,6,6-tetrachlorocyclohexanone onto which a radical is grafted (which is here represented by R and which corresponds to $R_1$ in the general formula) to form the corresponding alcohol with formation of the epoxide under the same conditions as above.

Equation 10 shows the opening of the epoxide 2h as obtained in equation 9. This opening with the HF/pyridine reactant takes place predominantly with the fluorine atom in a position cis to the hydroxyl group. The diastereoselectivity is in the ratio of 19 to 1 in the case of the fluorohydrins cis 1m/trans 1m'.

Equation 11 shows the preparation of the epoxides 2k, 2k', 2k'' from the mixture of the alcohols 1m, 1m' obtained in equation 10. The secondary product 2k' is a compound originating from the alcohol 1m.

Equations 12 and 13 show how it is possible to introduce an additional fluorine atom and to obtain, after the treatment with sodium hydroxide, the difluorinated epoxides 2l, 2l' and 2l'' in proportions which are unchanged in relation to the mixtures of the alcohols 2k, 2k' and 2k''. The predominant epoxide 2l which contains 2 fluorine atoms on the same carbon is in a ratio of 9 to 1 relative to the other two isomers.

Equations 14–18

These successions of opening and closing allow the substitutions of the halogens to be well controlled in a highly selective manner in relation to each other. This is perfectly exemplified by the inversion of the configuration shown in the equations of scheme III. In equations 14–17, the problem is to make a difluoro compound 1g containing a fluorine in position 6. This arrangement allows the aromatization to be made easier to give optionally substituted difluorobenzenes in better yields than when starting with the trifluoro compound 1d. The first reaction (equation 14) reiterates equation 3. The second (equation 15) is that of the action of boron trichloride on a mixture of epoxides 2b, 2b'. The predominant product obtained (equation 15) corresponds to the structure of the product 1b obtained in equation 2 of scheme 1 but in which the configuration has been inverted (hydroxyl and fluorine in trans position). The treatment of pure 1f to give the epoxide 2e (equation 16) and then its opening by the $BF_3.EtO_2$ reactant (equation 17) result in the pure product 1g which has a chlorine and a fluorine in position 2 and 6.

Equation 18 is a second example of inversion of the relative configuration of the fluorohydrin 1g (which has two fluorine atoms carried by the carbons 2 and 6, one being cis, the other trans to the hydroxyl group) into fluorohydrin 1h, where the two fluorine atoms are trans to the hydroxyl group.

Equation 19

Equation 19 shows how, by using boron tribromide, a bromine atom cis to the hydroxyl functional group of the alcohol 1i can be introduced, the treatment of which with sodium hydroxide makes it possible to obtain the α-bromoepoxide 2g.

Further, as mentioned above, another subject of the present application is a process permitting the aromatization of the ketones and alcohols according to the present invention.

Insofar as the aromatization of ketones is concerned, whether hydrated or not, it can take place according to the processes which are known to a person skilled in the art. However, according to the present invention, it has been shown that the treatment with basic aromatic nuclei such as pyridine and derivatives makes it possible to obtain an aromatic nucleus corresponding to the ketone.

Nevertheless, to dehydrate the hydrates and when aromatization involves a dehydration, it was desirable to employ dehydrating agents such as, for example, molecular sieves whose pore diameter is advantageously smaller than 1 nanometer (10 Å) in order to significantly improve kinetics and yield.

The aromatization of various hydrated ketones thus obtained results in the removal of an OH group on the central carbon (1) and the removal of halogen on each of the carbons which adjoin it.

The aromatization of ketones properly so-called can be carried out by heating solvent systems of a basic nature, broadly speaking, such as amines, amine salts, phosphines or amides, optionally in combination with salts, such as alkali metal halides like LiCl, or salts of weak acids, such as carbonates.

The leaving halogens leave proportionately more easily, the higher their atomic number. The removal of fluorines is particularly difficult and requires a significantly longer reaction time.

Thus, the ketone compounds according to the present invention make it possible to obtain easily, in a specific manner, 2,6-dihalogenated phenols in good yields.

To go from the alcohols, according to the present invention, to the corresponding ketones it is possible to employ known techniques such as those of Jones: Bowden, Heilbron, Jones, Weedon, *J. Chem. Soc.* 39, 1946 and Bowers, Halsall, Jones, Lemin, *J. Chem. Soc.* 2548, 1953, or Dess-Martin: C. W. Perkins, J. C. Martin, A. J. Arduengo, W. Lau, A. Alegria, J. K. Kochi, *J. Am. Chem. Soc.* 102, 7753, 1980 and D. B. Dess, J. C. Martin, *J. Org. Chem.* 48, 4155–56, 1953, or of Corey: *Pyridinium Chlorochromate* (Corey's reactant): Corey, Suggs, *Tetrahedron Lett.* 2647, 1975.

Scheme 5: Preparation of the tetrahalogenated hydrates and their dehydration to corresponding ketones.

Scheme 5: Preparation of the tetrahalogenated hydrates and of the corresponding ketones

EQUATION 20

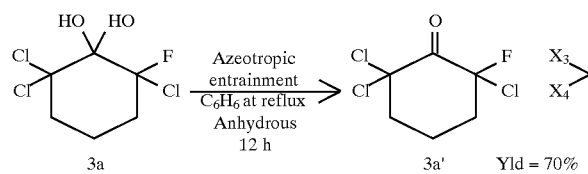

*Equation 21

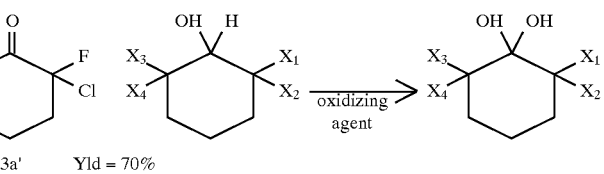

EQUATION 21*

| Initial alcohols | pyridinium chlorochromate PCC | | | Other oxidizing agents | | | 1,1-diols |
|---|---|---|---|---|---|---|---|
| | Time | Solvent and temperature | Yield | Time | Solvent and temp. | Yield | |
| 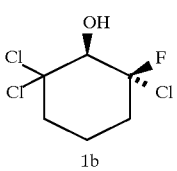 1b | 7 h | 1,2-Dichloroethane at reflux | 74% | 16 h | JONES acetone: 45–50° C. | 56% | 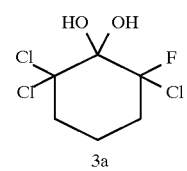 3a |

Scheme 5: Preparation of the tetrahalogenated hydrates and of the corresponding ketones

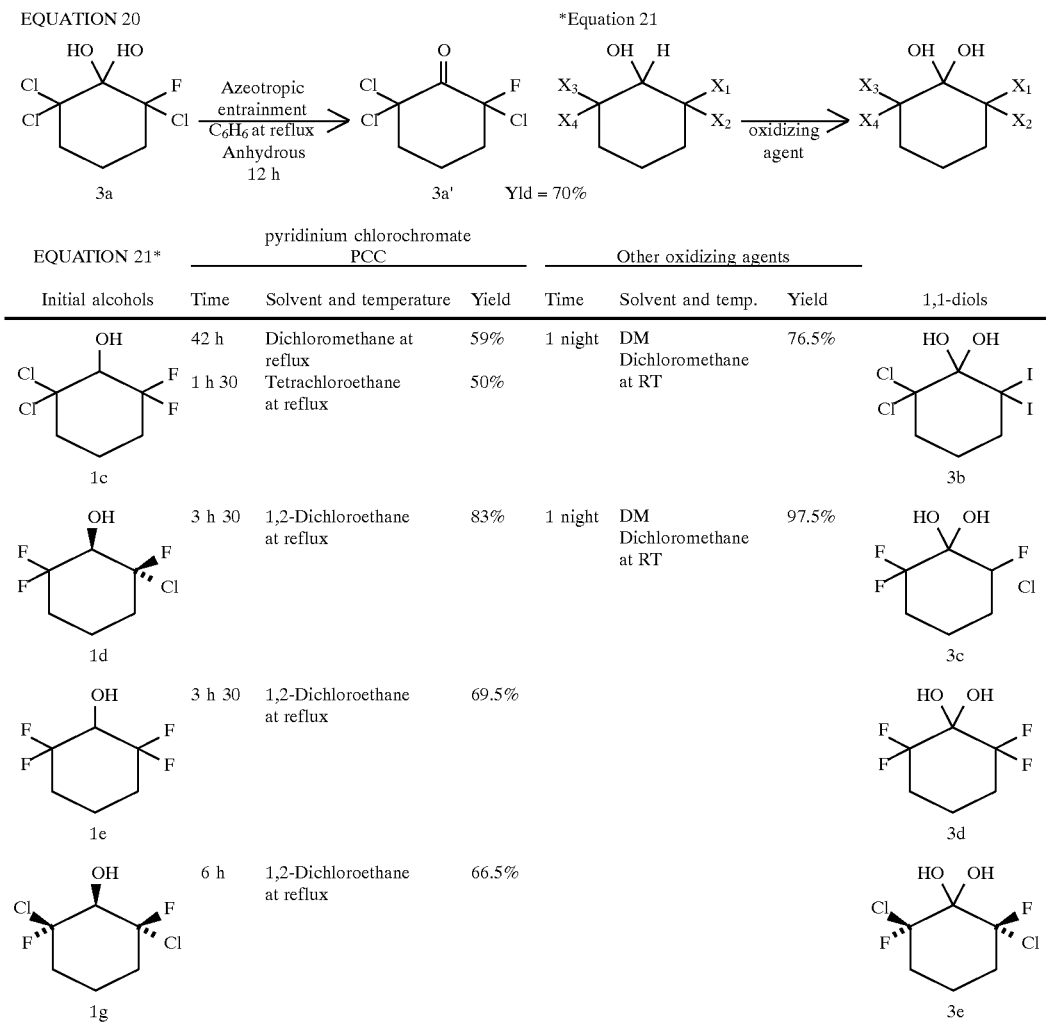

Scheme 5, equation 20 shows the step from the ketone hydrate to ketone by azeotropic entrainment in the presence of an aromatic solvent, preferably benzene or toluene.

Equation 21 shows the oxidations of the fluorohydrins 1b–1e and 1g to the corresponding hydrated ketones 3a–3e with the aid of the pyridinium chlorochromate, Jones and Dess-Martin reactants. Using this method, 2,2,6,6-tetrafluorocyclohexanone hydrate 3d is obtained in a 69.5% yield.

The ketone compounds may be modified to give rise to reaction intermediates which can be aromatized like the ketones; it is thus possible to go from a ketone compound to an equivalent such as, for example, thioketones, acetals, imines, oximes, double bonds obtained by acidic methylenes on ketones (for example by synthesis of the malonic type).

The ketones according to the invention can react with phenols to give compounds with mono- or disubstitution, compounds which are of interest, even without it being necessary to aromatize.

The reduction reactions (for example, LiAlH$_4$ in THF at reflux overnight) with imines make it possible to obtain aziridines which are particularly interesting synthesis intermediates; thus, in the compounds of the formula II, simple equivalents are compounds where nitrogen is substituted for oxygen.

The oxidation of the alcohol followed by its reduction can be envisaged to make it possible to obtain an alcohol or an alcohol mixture of different configuration from that at the outset. It is also possible to aromatize the alcohols directly to give an orthosubstituted phenol.

Thus, as mentioned above, another subject of the present application is a process permitting the aromatization of epoxides according to the present invention to give a meta-substituted phenol.

The conditions are analogous to those of the aromatization of alcohols or ketones; they are advantageously the following: heating to reflux in amine bases or amides; it should be noted, however, that when the amines have a replaceable hydrogen certain reactions other than, or in addition to, the aromatization can take place, especially the replacement of a halogen by the said amine.

Amides are, however, preferred. This aromatization makes it possible to obtain compounds substituted meta to a phenol functional group, that is to say that the aromatization results in a phenol functional group on one of the adjoining carbons (that is to say 2 or 6) carrying one of the arms of the epoxide bridge. The removal of the halogen on the other adjoining carbon takes place within the rules already referred to, that is to say that the halogen whose halide forms the least active leaving group remains. It is also possible to obtain a phenol when carbon 1 of the epoxide of formula (II) carries a hydrocarbon chain. Under these conditions a phenol ortho-substituted by the hydrocarbon chain and meta-substituted by a halogen is obtained.

Scheme 6: Aromatization reactions which make it possible to obtain stereoselectively mono- and disubstituted phenol derivatives.

Scheme 6: Aromatization reactions

EQUATION 22*

| SUBSTRATES | CONDITIONS | TIME | 4Å MOLECULAR SEIVE | Yield | PRODUCTS |
|---|---|---|---|---|---|
| $X_2 = X_3 = X_4 = Cl$ <br> $X_1 = F$ | 10 EQ. OF PYRIDINE AT REFLUX | 3 h 30 | YES | 79.5% | $X''_1 = F$ <br> $X''_3 = Cl$ <br> 4a |
| $X_1 = X_2 = F$ <br> $X_3 = X_4 = Cl$ | 10 EQ. OF PYRIDINE AT REFLUX | 3 h 30 | NO | <5% | $X''_1 = F$ <br> $X''_3 = Cl$ |
|  | 10 EQ. OF PYRIDINE AT REFLUX | 3 h 15 | YES | 75.5% | 4a |
| $X_1 = X_3 = X_4 = F$ <br> $X_2 = Cl$ | 10 EQ. OF PYRIDINE AT REFLUX | 15 h | YES | 20% | $X''_1 = X''_3 = F$ <br> 4b |
| $X_1 = X_4 = F$ <br> $X_2 = X_3 = Cl$ | 10 EQ. OF PYRIDINE AT REFLUX | 3 h 15 | YES | 71.5% | $X''_1 = X''_3 = F$ <br> 4b |

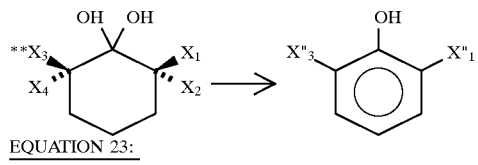

EQUATION 23:

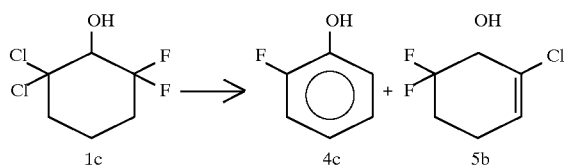

TEST 1 230–40° C.; 0.4 eq. DMAP; 6 h 4c yld = 14% 5b yld = 45% 
TEST 2 220–30° C.; 1 eq. DMAP; 19 h 4c yld = 30% 5b yld = 15% 
EQUATION 24 
EQUATION 24

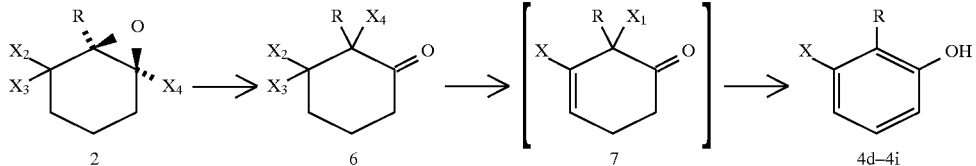

2 terms isolated:
6a: $X_1 = X_2 = X_3 = Cl$, R = allyl
6b: $X_1 = Cl$, $X_2 = X_3 = F$, R = Me

EQUATION 25*

| STARTING MATERIALS | REACTION CONDITIONS | TREATMENT | Yield | FINISHING PRODUCTS | GC PURITY |
|---|---|---|---|---|---|
| $R_1 = H$; $X_1 = Cl$ <br> $X_2 = Cl$; $X_3 = Cl$ | DMF at reflux; 3 h. | Acidifications with 3M HCl then flash | 83.5% | R = H <br> 4d | 95% |
| $R_1 = CH_3$; $X_1 = Cl$ <br> $X_2 = Cl$; $X_3 = Cl$ | DMF at reflux; 3 h. | Acidification with 3M HCl then flash | 89% | $R = CH_3$ <br> $X = Cl$ <br> 4e | >96% |
| $R_1 = CH_2 = CH$ <br> $X_1 = X_2 = X_3 = Cl$ | DMF at reflux; 3 h 30. | Acidification with 3M HCl then flash | 75.5% | $R = CH_2 = CH$ <br> $X = Cl$ <br> 4f | >99.5% |
| $X_1 = Cl$; $X_2 = Cl$; <br> $R = CH_2 = CH - CH_2$ | DMF at reflux; 5 h. | Acidification with 3M HCl; then 3M NaOH, extraction with $Et_2O$, then acidific with 3M HCl | 89% | $R = CH_2 = CH - CH_2$ <br> $X = Cl$ <br> 4g | >97% |
| $R_1 = CH_3$; $X_3 = Cl$; <br> $X_2, X_3 = F$; | DMF at reflux 3 h, then 2 eq. of DMAP reflux 3 h. | Acidification with 3M HCl; then flash | 22% | $R = CH_3$; $X = F$; <br> 4h | >93% |

-continued

Scheme 6: Aromatization reactions

| | | |
|---|---|---|
| $R_1$ = H; $X_2$ = Cl; $X_3$ = F; $X_1$ = Cl | DMF at reflux; 3 h. | Acidification with 3M HCl; then flash | 85% | R = H; X = F; 4i R = H; X = Cl 4d 4i/4d = 76/24 |

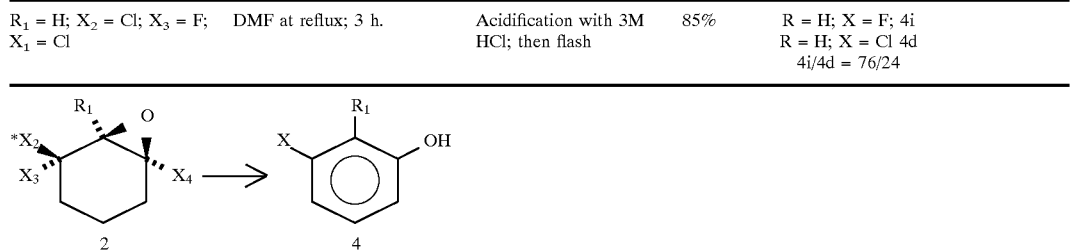

Scheme 6:

Equation 22 shows the conversion of the tetrahalogenated ketone hydrates 3a–c and 3e to 2,6-dihalogenated phenols 4a–4b. This reaction must be performed in the presence of a dehydrating agent, preferably 4 Å molecular sieves. Equation 23 shows the aromatization of the fluorohydrin 1c to 2-fluorophenol 4c. The formation of 2-fluorophenol 4c in this reaction is accompanied by the allyl alcohol 5b.

Equation 24 shows the intermediate formation of the 2,3,3-trihalogenated ketone 6 in the aromatization reaction of the epoxides 2 (R=alkyl). The β,γ-unsaturated dihalogenated ketone 7 is postulated as an intermediate stage giving access to the phenols 4. The metahalogenated phenols 4d–4i alkylated in position 2 (or carrying a hydrogen in this same position) were described in equation 25 and were obtained by heating the corresponding epoxides in dimethylformamide.

The following nonlimiting examples illustrate the invention.

EXAMPLE 1

Preparation of 1,3,3-trichloro-7-oxabicyclo[4.1.0]heptane 2a 7 g (175 mmol) of sodium hydroxide pellets were added in three portions at 10°–15° C. to 15.2 g (63.88 mmol) of 2,2,6,6-tetrachlorocyclohexanol 1a in suspension in 70 cm$^3$ of distilled water. The reaction mixture was kept at room temperature for 1 h 15 min, 20 cm$^3$ of ethyl ether were then added, stirring was continued for 5 min and then the phases were separated and the aqueous phase was extracted with ether (6×50 cm$^3$). The ether phases were combined, dried over MgSO$_4$, filtered, and the mixture was concentrated with a rotary evaporator. A liquid epoxide 2a (m=12.42 g) was obtained, representing 96.5% of the theoretical yield. The compound 2a will be frequently employed without further purification in the following stages (semicapillary GC purity>96%). The epoxide 2a can be purified by distillation at reduced pressure (boiling at 40° C. at 0.1 mm Hg); after distillation, the yield of compound 2a was 92%.

b.p.: 213° C.; $^1$H NMR (CDCl$_3$+3% TMS): 1.25–2.0 (m, 2 H); 2.0–2.8 (m, 4H); 3.8 (s, 1 H). $^{13}$C NMR (CDCl$_3$):84.37 (s, $C_3$); 73.36 (s, $C_1$); 65.50 (d, $C_2$); 38.70 (t, $C_4$); 31.49 (t, $C_6$); 18.51 (t, $C_5$); MW: 201.479; IR in cm$^{-1}$ (pure): 1080–1130; Microanalysis: $C_6H_7Cl_3O$; Calc. % C 35.77 H 3.50; F. % 35.83 3.57

EXAMPLE 2

Preparation of 3,3-dichloro-1-fluoro-7-oxabicyclo[4.1.0]heptane 2b

The same procedure as in Example 1 was applied to 2 g (9.03 mmol) of alcohol 1b in suspension in 12 cm$^3$ of distilled water and 1.5 g (37.5 mmol) of sodium hydroxide. Reaction time was 1 h 15 min. Ether extraction (5×25 cm$^3$). 1.61 g of crude product were obtained, the analysis of which by $^1$H NMR (80 MHz) showed the presence of the epoxides 2b and 2b' in a proportion 2b/2b'=93/7 (calculation by integration of the signals at 3.88 and 3.82 ppm, representing the proton carried by the carbon no. 2 of epoxide 2b and of its stereoisomer 2b'). The crude yield was 96%; the epoxide 2b was employed as such because of the impossibility of separating it easily from 2b'. $^1$H NMR (CDCl$_3$): 3.93 (d, 1H, $J_{HF}$=1.8 Hz); 2.47–1.38 (m, 6H).

IR (film) in cm$^{-1}$: 1180, 1085, 1040, 930, 890, 820, 770. $^{13}$C NMR (C$_6$D$_6$): 103, 52–89.66 (d, $C_1$, $J_1$=277, 2 Hz); 84.97 ($C_3$); 63.35–62.88 (d, $C_2$, $J_2$=10.5 Hz); 39.20 ($C_4$); 24.94–23.62 (d, $C_6$, $J_2$=25.9 Hz); 17.79–17.37 (d, $C_5$, $J_3$=8.4 Hz).

EXAMPLE 3

Preparation of 1-chloro-3,3-difluoro-7-oxabicyclo[4.1.0]heptane 2c

The same procedure as in Example 1 was applied to 0.6 g (2.93 mmol) of pure alcohol 1c in suspension in 5 cm$^3$ of distilled water and 0.48 g (≈12 mmol) of sodium hydroxide. Reaction time was 1 h 15 min. Ether extraction (5×15 cm$^3$). 0.43 g of a liquid, the epoxide 2c, were obtained, having a crude yield of 87%.

$^1$H NMR (CDCl$_3$): 3.56 (t, 1H, J=2.2 Hz); 2.79–1.32 (m, 6H). $^{13}$C NMR (C$_6$D$_6$): 131.9–120.1–108.2 (t, $C_3$), 65.8 ($C_1$); 61.18–59.17–57.13 (t, $C_2$); 32.42 ($C_6$); 30.81–29.66–28.47 (t, $C_4$); 17.09–16.87–16.06 (t, $C_5$). IR (film) in cm$^{-1}$: 1120, 1100, 975, 835; Microanalysis $C_6H_7ClF_2O$; F: % C 43.40 % H 4.19; Th: 42.75 4.19.

EXAMPLE 4

Preparation of 1,3,3-trifluoro-7-oxabicyclo[4.1.0]heptane 2d

The same procedure as in Example 1 was performed with 0.72 g (3.8 mmol) of pure trifluoro alcohol 1d, with 5 cm$^3$ of distilled water and 0.55 g (≈13.7 mmol) of sodium hydroxide. Reaction time was 1 h 15 min. Ether extraction (5×15 cm$^3$); 0.36 g of epoxide 2d were obtained, having a crude yield of 62%.

$^1$H NMR (CDCl$_3$): 3.61 (g, 1H, J=1.9 Hz); 2.40–1.45 (m, 6H). IR in cm$^{-1}$ (CDCl$_3$): 1460–1370–1250–1240–1210.

EXAMPLE 5

Preparation of 2,2,6-trichloro-6-fluorocyclohexanol (cis) 1b

Using HF/pyridine 3.2 cm³ of HF/pyridine were introduced (with a polyethylene syringe) into a polyethylene flask fitted with a bar magnet and a septum (the reaction medium having an exit towards the exhaust hood). The reaction mixture was taken to about −35° C. (external bath temperature) and 1.93 g (9.6 mmol) of epoxide 2a were added over 25 min by virtue of a syringe-driver. The materials were then left to react for 3 h at the same temperature and then returned to room temperature (30 min). The product was hydrolyzed with ice at 0° C., extracted with dichloromethane (5×20 cm³) dried over magnesium sulfate and filtered, and the solvents were evaporated. 2.03 g of an oil were collected, consisting of 85% of fluoro alcohol 1b and 15% of allyl alcohol 5a (calculation using ¹H NMR: integration of the proton at the bottom of the alcohol functional group of the compound 1b (d; 4.04 ppm, $J_1$=18.4 Hz) relative to the proton at the bottom of the alcohol functional group of the compound 5a (s, 4.36 ppm). Since the two alcohols 1b and 5a cannot be separated by distillation or flash chromatography on silica, a chemical purification of the alcohol 1b was employed. After this purification the yield of pure compound 1b was 82%, based on the starting epoxide 2a.

Using $BF_3.Et_2O$ 1 g (4.96 mmol) of predistilled epoxide 2a in solution in 7 cm³ of dichloromethane was introduced into a 25-cm³ round bottom flask. 0.325 cm³ (0.53 eq.) of $BF_3.Et_2O$ were added and the mixture was heated to reflux for 3 h (the end of the reaction was followed using GC). The product was hydrolyzed with 6N HCl (10 cm³) overnight, extracted with dichloromethane (5×30 cm³), dried over magnesium sulfate and the solvents were evaporated off. The oil obtained was incorporated onto silica and purified by flash chromatography (eluent: ether/petroleum ether=10/90); 1.01 g of a white solid was obtained, the monofluoro alcohol 1b. The reaction yield was 92%.

m.p.=37°–38° C. ¹H NMR (CDCl₃): 4.04 (dd, 1H, $J_{HF}$= 18.4 Hz, $J_{H—OH}$=9.6 Hz); 3.14 (d, 1H mobile, J=9.6 Hz); 2.96–1.49 (m, 6H). ¹³C NMR (C₆D₆): 118.78–106.06 (d, C₆, $J_{CF}$=254, 5 Hz); 91.62–91.52 (d, C₂, $J_{CF}$=1.9 HZ); 81.73–80.78 (d, C₁, $J_{CF}$=19 Hz); 44.67 (s, C₃); 40.08–38.96 (d, C5, $J_{CF}$=22.3 Hz); 19.59 (s, C₄). IR (in cm⁻¹) (CDCl₃): $v_{OH}$=3570; Microanalysis: C₆H₈OCl₃F; F. % C: 32.59 % H: 3.52; Th. 32.54 3.64

Characteristics of the allyl alcohol 5a

¹H NMR (CDCl₃): 5.97 (t, 1H); 4.36 (s, 1H). 3.1 (s, 1H mobile); 2.9–2.1 (m, 4H); ¹³C NMR (CDCl₃): 128.20 (s, C₂); 126.69 (d, C₃); (C—H coupling) 90.98 (s, C₆): 76.90 (d, C₁); 35.43 (t, C₅); 25.06 (t, C4). IR (CDCl₃) in cm⁻¹: $v_{OH}$=3580 (narrow band); C=C=1650.

EXAMPLE 6

Preparation of 2,2-dichloro-6,6-difluorocyclohexanol 1c

Using HF/pyridine 2.75 cm³ of HF/pyridine complex were introduced into a 20-cm³ polyethylene flask, with magnetic stirring, fitted with a septum and an exit towards the exhaust hood. 1.53 g (8.27 mmol) of epoxide 2b (containing 7% of the stereoisomer 2b') were added at 0° C. over 20 min, the mixture was left to react for 10 min and then returned to room temperature and stirring was continued for 50 min. Ten cm³ of distilled water were added at −10° C., the product was extracted with dichloromethane (5×20 cm³), dried over magnesium sulfate, filtered and evaporated down to obtain 1.67 g of crude product whose analysis by semicapillary GC revealed the presence of two stereoisomers 1c and 1c' in a proportion of 93/7. The purification can be carried out in two different ways:

By flash chromatography on silica (possible separation of 1c and 1c'): in a first test the mixture of the alcohols 1c and 1c' was isolated in an 86% yield (eluent: ether/petroleum ether=90/10).

In a second test the separation conditions were modified (eluent: ether/petroleum ether=96/4), thus giving 1.2 g (yld= 71%) of alcohol 1c (semicapillary GC purity>98.5%) and 0.2 g (yld=12%) of the alcohols 1c and 1c' in a proportion of 82/18.

In order to characterize the structure of the alcohol 1c unambiguously, the quantities of starting material were increased (≈10 g of epoxide 2b) and in this way it was possible to isolate, in addition to the alcohol 1c, 200 mg of alcohol 1c' of a semicapillary GC purity>98.5% after three flash chromatographies on silica.

Using $BF_3.Et_2O$

The same procedure was employed as for the production of 1b in Example 5: performed on 1.35 g of the epoxides 2b and 2b' (2b/2b'=93/7) in solution in 10 cm³ of 1,2-dichloroethane and 0.26 cm³ (0.55 eq.) of $BF_3.Et_2O$; reflux time 1 h 45 min. The product was hydrolyzed with 10 cm³ of water overnight. The purification was performed as previously (column 0=2 cm, h=9 cm, eluent: ether/petroleum ether=10/90). 1.23 g of a colorless liquid, the difluoro alcohol 1c (mixed with 7% of alcohol 1c') were obtained. The overall reaction yield was 82%.

Alcohol 1c

¹H NMR (CDCl₃): 3.99 (dd, 1H, $J_1$=15.95 Hz, $J_2$=6.4 Hz); 3.14 (s, 1H mobile); 2.93–1.18 (m, 6H). ¹³C NMR (C₆D₆): 132.85–120.54–108.07 (t, C₆); 91.35–90.98 (d, C₂, $J_3$=7.4 Hz); 78.35–77.73–76.46 (dd, C₁); 42.84 (C₃); 32.43–31.29–30.13 (t, C₅); 18.75–18.67 (d, C₄, $J_3$=1.6 Hz). IR (pure) in cm⁻¹: $v_{OH}$=3550 (narrow); 3450 (broad). Microanalysis C₆H₈Cl₂F₂O; F. % C 34.94 % H 3.86 Th. 35.15 3.93

Alcohol 1c' m.p.=80°–81° C.; ¹H NMR (CDCl₃): 3.93(dt, 1H, $J_1$=20.6 Hz, $J_2$=9.6 Hz); 2.93 (d, 1H mobile, J=9.6 Hz); 2.85–1.45 (m, 6H). ¹³C NMR (CDCl₃): 111.64 (d, C₁, J=254.3 Hz); 79.50 (t, C₂ and C₆, J=19.7 Hz); 39.46 (t, C₃ and C₅, J=11.3±0.5 Hz); 18.58 (S, C₄). IR (CDCl₃) in cm⁻¹: $v_{OH}$= 3450 cm⁻¹ (broad). Microanalysis: C₆H₈Cl₂F₂O; F. % C 34.98 % H 3.82; Th. % C 35.15 % H 3.93

EXAMPLE 7

Preparation of 2-chloro-2,6,6-trifluorocyclohexanol 1d

Using HF/Pyridine 3 cm³ of HF/pyridine complex were introduced into a 10-cm³ polyethylene bottle equipped with a septum, an exit towards the exhaust hood and with magnetic stirring. 1.23 g (7.30 mmol) of chloroepoxide 2c were added over 25 min at 0° C., the mixture was left to react for 10 min and then returned to room temperature and the stirring was continued for 1 h 20 min. 7 cm³ distilled water were added at 0° C., the product was extracted with dichloromethane (5×15 cm³), dried over magnesium sulfate and filtered, and the solvent was evaporated off. The crude product obtained (1.25 g) was purified by flash chromatography on silica; column: O=2.8 cm, h=13 cm, eluent: ether/petroleum ether=10/90 to 12/88. 0.16 g (0.85 mmol) of pure diastereoisomer 1d were isolated, together with 0.8 g (4.24 mmol) of mixture of 1d and 1d' (in a proportion 1d/1d'=95/5 determined by semicapillary GC) and 0.19 g (1.01 mmol) of pure diastereoisomer 1d'. The overall reaction yield was 83.5%, the overall proportions 1d/1d' (as isolated products) were approximately 83/17.

Using BF$_3$.Et$_2$O

The same procedure was employed as for the production of 1b in Example 5: performed on 0.39 g (2.31 mmol) of epoxide 2c in solution in 3.3 cm$^3$ of dichloromethane and 0.16 cm$^3$ (0.55 eq.) of BF$_3$.Et$_2$O; reflux time: 1 h 30 min. The product was hydrolyzed with 5 cm$^3$ of 6N HCl overnight. The purification was performed as previously (eluent: ether/petroleum ether=10/90) and made it possible to isolate 0.36 g of trifluoro alcohol 1d containing no 1d', isomer, according to semicapillary GC. The reaction yield was 82.5%.

Alcohol 1d m.p. °C.=42–43. $^1$H NMR (CDCl$_3$): 3.98 (d, t, 1H, J=16.6 Hz, J=5.1 Hz); 3.10 (s, 1H mobile) 2.80–1.50 (m, 6H). $^{13}$C NMR (C$_6$D$_6$): 120.95 (t, C$_6$, J=246.6 Hz); 94.6 (d, C$_2$, J=246.6 Hz ); 77.49–76.5275.18–74.21–(q, C$_1$); 37.61 (d, C$_3$, J=22 Hz); 31.36 (t, C5, J=22 Hz); 17.52 (s, C4). IR in cm$^{-1}$ (film); $v_{OH}$=3400. Microanalysis: C$_6$H$_8$ClF$_3$O.

Alcohol 1d'

Th. % C 33.21 % H 4.28; F. 38.30 4.11; $^1$H NMR (CDCl$_3$): 4.22–3.78 (m, 1H); 2.75 (d, 1H mobile, J=6 Hz) 2.65–1.53 (m, 6H). IR (pure) in cm$^{-1}$: $v_{OH}$=3440 cm$^{-1}$ (broad). $^{13}$C NMR (CDCl$_3$): 122.71 (t, C$_6$, J=232±8 Hz); 114.73 (d, C$_2$, J=246.6 Hz) 75.94; 74.60; 73.27; 71.93 (q, C$_1$); 35.99 (d, C$_3$, J=19.53 Hz); 29.44 (t, C$_5$, J=23±1 Hz); 17.55 (t, C$_4$, J=4.88 Hz).

EXAMPLE 8

Preparation of 2,2,6,6-tetrafluorocyclohexanol 1e

The same procedure was employed as for the production of 1b in Example 5: performed with 0.3 cm$^3$ of HF/pyridine complex per 0.09 g (0.59 mmol) of epoxide 2d in solution in 0.1 ml of THF (addition with syringe-driver over 10 min at 0° C. and then allowed to return to room temperature 1 h). 3 cm$^3$ of distilled water were added at 0° C. and the mixture was extracted with dichloromethane (3×10 cm$^3$).

After flash chromatography on silica (eluent: ether/ petroleum ether=30/70) 0.05 g (0.29 mmol) of a white solid, the alcohol 1e, were isolated in a 49% yield.

m.p. °C.=65–66. $^1$H NMR (CDCl$_3$) 400 MHz: 4.00–3.85 (m, 1H); 2.61 (d, 1H mobile, J=1 Hz); 2.25–2.05 (m, 2H); 1.98–1.78 (m, 2H); 1.78–1.63 (m, 2H). IR in cm$^{-1}$ (CDCl$_3$): $v_{OH}$=3590; $^{13}$C NMR (CDCl$_3$) 100 MHz: 120.89 (t, C$_2$ and C$_6$, J=248 Hz); 71.72 (m, C$_1$) 29.96 (t, C$_3$ and C$_5$, J=22.5 Hz); 16.18 (d, C$_4$, J=5.4 Hz).

EXAMPLE 9

Preparation of 2,2,6-trichloro-6-fluoro-1,1-cyclohexane-diol 3a

Using PCC (pyridinium chlorochromate)

0.96 g (4.33 mmol) of trichlorofluoro alcohol 1b in solution in 10 cm$^3$ of dichloroethane were introduced into a 25-cm$^3$ round bottom flask fitted with a condenser and with magnetic stirring. 2.33 g (2.5 eq.) of PCC were added with a spatula and the mixture was heated to reflux under argon atmosphere for 7 h. The reaction mixture was allowed to cool and was then taken up with 100 cm$^3$ of ether, the whole being filtered on florisil. The solvents were evaporated off, the residue was incorporated on silica and purified by flash chromatography (eluent: ether/petroleum ether=15/85 then 20/80). 0.03 g of starting alcohol 1b, that was approximately 3%, and 0.05 g of a mixture of alcohol 1b, diol 3a and 0.76 g of pure diol 3a were isolated. The yield of compound was therefore higher than 74%.

Using the Jones reactant

The composition of the Jones reactant was as follows: 6.7 g of CO$_3$, 14.5 ml of distilled water, 5.8 ml of 98% H$_2$SO$_4$.

0.5 g (2.26 mmol) of alcohol 1b in solution in 3 cm$^3$ of acetone were introduced into a 10-cm$^3$ round bottom flask fitted with a condenser and with magnetic stirring. 5 cm$^3$ of the Jones reactant were introduced gently; the reaction was highly exothermic; the reaction mixture was then heated to 45°–50° C. for 16 h (1 cm$^3$ of Jones reactant having been added after 4 h and 2 cm$^3$ after 9 h of reaction). At the end of reaction the Jones reactant was destroyed with 10 cm$^3$ of isopropanol, the mixture was diluted with 10 cm$^3$ of water, extracted with dichloromethane and dried over magnesium sulfate, and the solvents were evaporated off. The material was incorporated onto silica and purified by flash chromatography. 0.16 g of starting alcohol 1b (32%) and 0.30 g of pure diol 3a were isolated, that was a 56% yield of compound 3a (Yld based on the unrecovered alcohol 1b =85%). m.p.=42°–43° C. $^1$H NMR (CDCl$_3$): 3.75 (s, 1H mobile); 3.60 (s, 1H mobile); 2.70–1.40 (m, 6H). IR in cm$^{-1}$ (CDCl$_3$): $v_{OH}$=3540 (very broad). Microanalysis: C$_6$H$_8$Cl$_3$FO; Th.: % C 30.34 % H 3.39; F.: 30.26 3.15

EXAMPLE 10

Preparation of 2,2-dichloro-6,6-difluoro-1,1-cyclohexane-diol 3b

First procedure: 0.5 g (2.44 mmol) of alcohol 1c in solution in 20 ml of dichloromethane were introduced into a 50-cm$^3$ three-necked flask fitted with a thermometer, a condenser and with magnetic stirring. 1.76 g (16.42 mmol) of magnesium sulfate and 2.10 g (9.75 mmol) of pyridinium chlorochromate were added while vigorous stirring was maintained. The mixture was heated to reflux under argon atmosphere for 42 h. The end of the reaction was verified by thin layer chromatography. The reaction mixture was then taken up with ether and filtered on florisil, the solvents were then evaporated off and the crude product was purified by flash chromatography on silica. 0.32 g (1.44 mmol) of diol 3b were isolated (Yld=59%), which can be distilled and which melts at about 30° C. It should be noted that the compound 3b was sublimed in the desiccator.

Second procedure: the same procedure was followed as in the first, except with tetrachloroethane; the material was heated to reflux (127° C.) for 1 h 30 min, after which time the presence of alcohol 1c was no longer detected by thin layer chromatography. The material was filtered on florisil, rinsed with ether, and evaporated down. The crude product was distilled under partial vacuum (water pump). The first fraction was tetrachloroethane (b.°C.=45/13 mm Hg). The diol 3b was then isolated by flash chromatography on silica (eluent: ether/petroleum ether=15/85 to remove the remaining tetrachloroethane then 25/75 to obtain the diol 3b). A 50% yield of diol 3b was obtained.

Oxidation using Periodinane (Dess-Martin reactant)

6.2 g (≈2.5 eq.) of Dess-Martin reactant were added to 1.14 g (5.56 mmol) of alcohol 1c in solution in 20 ml of dichloromethane. The reaction mixture was magnetically stirred overnight at room temperature. 100 cm of ether were then added and the mixture was poured into 150 cm$^3$ of a 0.52M solution of Na$_2$S$_2$O$_3$, saturated with NaHCO$_3$; after settling, the organic phase was separated from the aqueous phase, which was reextracted with 2 times 25 cm$^3$ of ether. The solution was dried over MgSO$_4$ and then evaporated down. After filtration on silica 0.94 g of diol 3b were obtained, which was a 76.5% yield.

m.p.=30° C. $^1$H NMR (CDCl$_3$): 3.75 (s, 2H mobile); 2.62–1.71 (m, 6H). $^{13}$C NMR (CDCl$_3$): 119.85 (t, C$_6$, J=253.91 Hz); 93.39 (t, $C_1$, J=24.41 Hz); 92.90 (s, $C_2$); 41.91 (s, $C_3$); 29.77 (t, $C_5$, J=21.97 Hz); 17.75 (t, $C_4$, J=4.88 Hz). IR in $cm^{-1}$ (film): $\nu_{OH}$=3700–3000 ($\nu_{C=O}$=1770)

EXAMPLE 11

Preparation of 2-chloro-2,6,6-trifluoro-1,1-cyclohexane-diol 3c

Using PCC.

The same procedure was employed as for the production of 3a in Example 9: performed with 0.60 g (3.18 mmol) of trifluoro alcohols 1d and 1d' (in a proportion 1d/1d'=95/5) in solution in 10 $cm^3$ of dichloroethane and 1.90 g (2.77 eq.) of PCC. The mixture was heated to reflux for 3 h 30 min; after treatment on florisil, 0.54 g (2.62 mmol) of crude diol 3c were obtained, which was an 83% yield of compound 3c.

Using the Dess-Martin reactant 6 g (2.5 eq.) of Dess-Martin reactant were added at room temperature to 1.02 g (5.41 mmol) of alcohol 1d in solution in 20 $cm^3$ of dichloromethane. The reaction mixture was left at room temperature overnight. 100 $cm^3$ of ether were then added and the whole was poured into 150 $cm^3$ of a 0.6M solution of $Na_2S_2O$ saturated with $NaHCO_3$. After settling, the ether and aqueous phases were separated, and a new extraction with 3×20 $cm^3$ of ether was carried out.

The organic phases were combined and after drying over $MgSO_4$ the solvents were evaporated off. 1.08 g of crude diol 3c were then obtained, which was a 97.5% yield.

m.p.°C.=35–36. $^1H$ NMR ($CDCl_3$): 3.66 (s, 2H mobile); 2.65–1.50 (m, 6H) IR in $cm^{-1}$ ($CDCl_3$): $\nu_{OH}$=3560 (very broad).

EXAMPLE 12

Preparation of 2,2,6,6-tetrafluoro-1,1-cyclohexanediol 3d

Using PCC

The same procedure was employed as for the production of 3a in Example 9: performed on 0.04 g (0.23 mmol) of tetrafluoro alcohol 1e in solution in 3 $cm^3$ of dichloroethane and 0.20 g (0.92 mmol) of PCC. The mixture was heated to reflux for 3 h 30 min and, after treatment on florisil, then washed with pentane. 0.03 g (0.16 mmol) of a white solid, the tetrafluorodiol 3d, were obtained.

The yield of product 3d was 69.5%. m.p.°C.=107–108. $^1H$ NMR ($CDCl_3$): 3.41 (s, 2H mobile); 2.60–1.45 (m, 6H); IR ($CDCl_3$) in $cm^{-1}$: $\nu_{OH}$=3570 (broad). MW=188.123. $^{13}C$ NMR ($CDCl_3$) 100 MHz: 119.97 (t, $C_2$ and $C_6$, J=252.15±0.75 Hz); 91.36 (t, $C_1$, J=26.32 Hz); 29.8 (m, $C^3$ and $C_5$); 15.5 (s, $C_4$). Microanalysis: $C_6H_8F_4O_2$; Th. % C 38.31 % H 4.29; F. 38.05 4.24

EXAMPLE 13

Preparation of 2-chloro-6-fluorophenol 4a

From the diol 3a 0.51 g (2.15 mmol) of diol 3a in solution in 1.65 $cm^3$ (≈10 eq.) of pyridine were heated to reflux for 3 h 20 min under argon atmosphere in the presence of 1.4 g of 4 Å molecular sieve in a 10-$cm^3$ round bottom flask fitted with a condenser. At the end of reaction the mixture was acidified to pH 1 with 10 $cm^3$ of 6N hydrochloric acid, was extracted with ether (5×20 $cm^3$), was dried over magnesium sulfate and filtered, and the solvent was evaporated off. A crude solid was obtained, which was purified by flash chromatography on silica (eluent: ether/pentane ether=10/90). 0.25 g (1.7 mmol) of a white solid with a strong phenolic odor, 2-chloro-6-fluorophenol 4a, were obtained. Yld=79.5%.

From the diol 3b 0.34 g (1.54 mmol) of diol 3b in solution in 1.2 $cm^3$ (10 eq.) of pyridine were heated to reflux for 3 h 15 min in the presence of 1 g of 4 Å molecular sieve and under argon atmosphere in a 10-$cm^3$ round bottom flask. The reaction was checked by capillary GC. At the end of reaction the mixture was acidified with 8 $cm^3$ of 4N hydrochloric acid, was extracted with dichloromethane (5×10 $cm^3$ and dried over magnesia sulfate, and the solvent was evaporated off.

0.19 g of a crude oil were obtained and purified by flash chromatography on silica (eluent: ether/pentane=10/90). 0.17 g (1.16 mmol) of a white solid, 2-chloro-6-fluorophenol 4a, were collected (Yld=75.5%).

m.p.°C.=64. $_1H$ NMR ($CDCl_3$): 7.30–6.60 (m, 3H); 5.55 (s, 1H mobile). IR in $cm^{-1}$ ($CDCl_3$): $\nu_{OH}$=3540 $\nu_{C=C}$=1600. Microanalysis: $C_6H_4ClFO$ Th.: % C 49.18 % H 2.75 F.: 48.95 2.57

EXAMPLE 14

Preparation of 2,6-difluorophenol 4b

From the diol 3c

The same procedure was employed as for the production of 4a in Example 13: it was performed on 0.40 g (1.94 mmol) of trifluorodiol 3c, 10 equivalents of pyridine (that was approximately 1.56 $cm^3$), 1 g of 4 Å molecular sieve; 15 h reflux. After purification as in Example 13 above, 0.05 g (0.38 mmol) of 2,6-difluorophenol 4b were isolated (eluent: ether/petroleum ether=10/90), which was checked by semi-capillary GC with the commercial product 4b from Aldrich (26,446-6). The yield of compound 4b was 20%.

From the diol 3e

The same procedure was employed as for the production of 4a in Example 13: performed on 0.69 g (3.12 mmol) of difluorodiol 3e, 10 equivalents of pyridine (≈2.5 $cm^3$), 2 g of 4 ∈ molecular sieve; 3 h 15 min reflux. After purification (as for 4a), 0.29 g of phenol 4b were isolated (eluent: ether/pentane=8/92).

The product obtained was checked by semicapillary GC with the commercial Aldrich product (26,446-6). The yield of compound 4b was 71.5%.

m.p.°C.=38–41. $^1H$ NMR ($CDCl_3$): 7.2–6.5 (m, 3H); 4.7 (s, 1H mobile). IR ($CDCl_3$) in $cm^{-1}$: $\nu_{OH}$=3570 (broad); $\nu_{C=C}$=1610. Reference: Aldrich 26,446-6

EXAMPLE 15

Preparation of 2-fluorophenol 4c

First Procedure: 0.11 g (0.2 eq.) of DMAP were added with a spatula to 0.95 g (4.63 mmol) of alcohol 1c, and the mixture was heated for 1 h 30 min to 230°–240° C. (external bath), 0.11 g (0.2 eq.) of DMAP were added and the mixture was heated again to the same temperature for 4 h 30 min. After cooling, the mixture was treated with 10% HCl to pH=1, extracted with ether, dried over magnesium sulfate, filtered and evaporated down. The crude product was purified by flash chromatography on silica (eluent: ether/petroleum ether=9/91). 0.2 g of 2-fluorophenol 4c (Yld=14%) and 0.35 g of fluoro allyl alcohol 5b (Yld=45%) were isolated.

Second Procedure: 0.30 g (1 eq.) of DMAP were added to 0.5 g (2.44 mmol) of alcohol 1c. The reaction mixture was stirred until dissolved (15 min) and then heated to 220°–230° C. for 19H. It was treated with 10% hydrochloric acid to pH=1, extracted with ether, dried over magnesium sulfate, filtered and evaporated down; the crude product was purified by flash chromatography on silica (eluent: ethyl acetate/petroleum ether=4.5/95.5). 0.08 g (0.73 mmol) of 2-fluorophenol 4c (Yld=30%) and 0.06 g (0.37 mmol) of allyl alcohol 5b (Yld 15%) were obtained.

d=1.256, b.p.°C.=171°–172°/741 mm Hg, m.p.°C.=16.1; $^1$H NMR (CDCl$_3$): 7.30–6.55 (m, 4H); 5.27 (s, 1H mobile). IR in cm$^{-1}$ (film): $\nu_{OH}$=3690–3000 $\nu_{C=C}$=1595–1620. Reference: Aldrich F1,280-4.

Allyl alcohol 5b $^1$H NMR (CDCl$_3$): 6.00–5.85 (t, 1H); 4.25–4.00 (t, 1H); 3.80–3.35 (s, 1H mobile); 2.45–1.65 (m, 4H). $^{13}$C NMR (CDCl$_3$): 128.42 (s, C$_2$); 127.70 (s, C$_3$); 121.22 (t, C$_6$, J=244 Hz); 70.83 (t, C$_1$, J=30.9 Hz); 25.04 (t, C$_5$, J=24 Hz); 22.72 (t, C$_4$, J=4 Hz);

EXAMPLE 16

Preparation of 2,2,6-trichloro-6-fluorocyclohexanol (trans) 1f 36 cm$^3$ of boron trichloride in molar solution in dichloromethane (36 mmol) were introduced at 4° C. under argon atmosphere into 12.12 g (65.50 mmol) of epoxide 2b (containing 7% of its stereoisomer 2b') in solution in 80 cm$^3$ of anhydrous dichloromethane. The reaction mixture was then allowed to return to room temperature and stirring was continued for 1 h. The mixture was hydrolyzed with 75 cm$^3$ of distilled water and extracted (4×50 cm$^3$) with dichloromethane, the organic phases were combined and dried over MgSO$_4$ and were evaporated down. The crude product obtained contained the diastereoisomeric alcohols 1f and 1b in a proportion 1f/1b=93/7 (determination by macrobore GC). Purification was carried out using flash chromatography on silica (eluent: ether/petroleum ether=4/96). 10.73 g (yld=74%) of pure alcohol 1f and 1.65 g (yld=11%) of a mixture of the alcohols 1f and 1b in a proportion 1f/1b=90/10 were isolated. The overall reaction yield was 85.5%.

Characteristics of the diastereoisomer 1f:

MW: 221.486; $^1$H NMR: 4.15 (t, 1H, J=7.6 Hz); 3.10 (d, 1H mobile, J=7.6 Hz); 2.86–1.67 (m, 6H). $^{19}$F NMR: –98 (s, 1F); IR in cm$^{-1}$ (film): $\nu_{OH}$=3510; MS (m/e): EI (30 eV): 226–224–222–220 (M+, 0.4–2.6,–8.2–8.5); 208–206–204–202–(0.4–3.1–10.2–11.3); 188–186–184 (5.1–25.3–39.1): 156 (22.8); 155 (23.2); 154 (35.8); 153 (33.5); 149 (19.1); 124 (18.5); 122 (50.1); 120 (81.2); 112 (24.5); 110 (34.6); 109 (17.1); 106 (15.5); 101 (33.4); 93 (49.3); 91 (100.0); 85 (41.5); 75 (85.68); 65 (30.6); 59 (17.7). Microanalysis: C$_7$H$_9$Cl$_3$FO F. % C 32.62 H 3.69; Calc. % 32.53 3.64

EXAMPLE 17

Preparation of 1,3-dichloro-3-fluoro-7-oxabicyclo [4.1.0]heptane 2e 0.85 g (21.3 mmol) of sodium hydroxide pellets were added in three portions to 1.6 g (7.22 mmol) of pure alcohol 1f in suspension in 22 cm$^3$ of distilled water at 15°–20° C. The reaction mixture was kept at room temperature for 1 h 15 min, 10 cm$^3$ of ether were then added, stirring was continued for 5 min and then the aqueous phase was separated off and extracted with ether (5×25 cm$^3$). The ether phases were combined, dried over magnesium sulfate and filtered, and the solvent was evaporated off. 1.28 g of a liquid, the epoxide 2e, were obtained; the crude yield was 96% (macrobore GC purity>98%).

MW: 185.026; $^1$H NMR: 3.69 (d, 1H, J$_{HF}$=4.3 Hz); 2.80–1.10 (m, 6H). IR in cm$^{-1}$ (film): 1410–1130–1110–1090–1080–920–870–845–820–790. MS (m/e) 30 ev EI: 151–149 (M+ —Cl, 16.9–54.8); 124 (8.3); 122 (15.0); 121 (8.8); 120 (8.3); 112 (29.9); 110 (44.8); 109 (7.6); 108 (13.3); 107 (12.6); 106 (39.0); 103 (7.9); 101 (24.3); 93 (33.7); 91 (32.8); 86 (8.7); 85 (63.4); 75 (100.0); 65 (26.6); 59 (29.0); 55 (20.9). Microanalysis: C$_6$H$_7$Cl$_2$FO; F. % C 38.76 H 3.76; Calc. % 38.95 3.81

EXAMPLE 18

Preparation of 2,6-dichloro-2,6-difluorocyclohexanol 1q 0.47 cm$^3$ (0.55 eq.) of BF$_3$.Et$_2$O were added to 1.89 g (7.03 mmol) of epoxide 2e in solution in 20 cm$^3$ of 1,2-dichloroethane. The reaction mixture was heated to reflux under argon atmosphere for 1 h 45 min and then hydrolyzed hot with 30 cm$^3$ of distilled water (stirring was continued for 10 min). It was extracted with dichloromethane (4×15 cm$^3$) and then dried over MgSO$_4$, filtered and evaporated down. 1.43 g of alcohol 1g were obtained, the macrobore GC purity of which was higher than 97%. The yield of alcohol 1g was 98%.

MW: 205.033; $^1$H NMR: 4.07 (dt, 1H, J$_{HF}$=8.3 Hz, J=8.5 Hz); 3.07 (s, 1H mobile, J=8.5 Hz); 2.90–1.40 (m, 6H). IR in cm$^{-1}$ (film): $\nu_{OH}$=3530,3420; MS (m/e) EI 30 eV: 208–206–204 (M+, 0.66–3.35–5.17); 190–188–186 (0.43–2.81–4.54); 170–168 (7.1–20.9); 139 (10.9); 138 (19.7); 137 (2.8.4); 133 (14.5); 129 (10.2); 122 (10.3); 121 (15.3); 120 (25.2); 113 (16.1); 106–104 (18.2–52.6); 96 (10.6); 94 (16.1); 93 (29.7); 91 (31.5); 88 (17.4); 85 (64.7); 75 (100.0); 65 (20.9); 59 (34.1).

EXAMPLE 19

Preparation of 2,6-dichloro-2,6-difluoro-1,1-cyclohexanediol 3e 4.03 g (18.69 mmol) of PCC were added with a spatula to 1.41 g (7.48 mmol) of alcohol 1g in solution in 25 cm$^3$ of dichloroethane (while keeping the reaction mixture vigorously stirred). The mixture was heated to reflux for 6 h, allowed to cool, taken up with ether and filtered on florisil. The solution obtained was evaporated down and the product obtained incorporated onto silica. It was purified by flash chromatography on silica (eluent: ether/petroleum ether=10/90 then 20/80): a first fraction was obtained, containing 0.24 g of starting alcohol 1g (17%) and a second one, containing 1.01 g of the expected 1,1-diol 3e. The yield of product 1g was 66.5%.

MW: 221.03; $^1$H NMR: 3.96 (s, 2H mobile S, J=8.5 Hz); 2.70–1.60 (M, 6H). IR in cm$^{-1}$ (pure film): $\nu_{OH}$=3520 (very broad). $^{13}$C NMR (CDCl$_3$) 20 MHz: 110.58 (d, C$_2$ and C$_6$; J=251.4 Hz); 91–31 (t, C$_1$, J=22.1 Hz); 35.61 (d, C$_3$ and C$_5$, J=22 Hz); 17.51 (d, C$_4$, J=4.9 Hz). Microanalysis: C$_6$H$_8$Cl$_2$F$_2$O$_2$; F. % C 32.15 H 3.79; Calc. % 32.60 3.65

EXAMPLE 20

Preparation of 3-chloro-1,3-difluoro-7-oxabicyclo [4.1.0]heptane 2f

The same procedure was employed as for the preparation of 2e in Example 17: it was performed with 0.18 g (0.88 mmol) of pure alcohol 1c, 3 cm of distilled water and 0.12 g (3 mmol) of sodium hydroxide, reaction time was 1 h 15 min; ether extraction (3×12 cm). After treatment, 0.13 g of epoxide 2f were obtained (macrobore GC purity>98%). The yield of epoxide 2f was 81%.

EXAMPLE 21

Preparation of 2,6-dichloro-2,6-difluorocyclohexanol 1h 0.36 cm$^3$ (0.55 eq.) of BCl$_3$ in molar solution in dichloromethane were added at 4° C. under argon atmosphere to 0.11 g (0.65 mmol) of epoxide 2f in solution in 3 cm$^3$ of dichloromethane. The reaction mixture was allowed to return to room temperature (1 h), 3 cm$^3$ of distilled water were then added and the mixture was extracted with dichloromethane (4×10 cm$^3$). The extract was dried over MgSO$_4$, filtered and evaporated down. The crude product was purified by flash chromatography on silica (eluent ether/petroleum ether=5/95). 0.08 g of alcohol 1h were obtained having a 60% yield (macrobore GC purity>95%).

MW: 205.033; $^1$H NMR: 4.08 (q, 1H, J$_{HF}$=5 Hz); 2.82 (s, 1H mobile, J=5 Hz); 2.70–1.35 (m, 6H).

EXAMPLE 22

Preparation of 2-bromo-2,6-dichloro-6-fluorocyclohexanol 1i 2.91 cm$^3$ (2.91 mmol) of BBr$_3$ in molar solution in dichloromethane were introduced at 4° C. under argon atmosphere into 0.98 (5.3 mmol) of epoxide 2e in solution in 6.5 cm$^3$ dichloromethane. The reaction mixture was then allowed to return to room temperature and stirring was continued (1 h 30 min). 5 cm$^3$ of distilled water were then added and the mixture was extracted with dichloromethane (4×10 cm$^3$). The extract was dried over MgSO$_4$, filtered and evaporated down. The crude product was purified by flash chromatography on silica (eluent ether/petroleum ether=5/95): 1.03 g of alcohol 1i were obtained (macrobore GC purity>97%); the yield of product 1i was 73%.

MW: 265.943; $^1$H NMR: 4.05 (t, 1H, J=6.3 Hz); 3.17 (s, 1H mobile, J=6.3 Hz); 3.00–1.50 (m, 6H). IR in cm$^{-1}$ (film): $v_{OH}$=3495.

EXAMPLE 23

Preparation of 1-bromo-3-chloro-3-fluoro-7-oxabicyclo[4.1.0]heptane 2g

The same procedure was followed as for the production of 2e in Example 17: it was performed with 0.20 g (0.75 mmol) of alcohol 1i, 3 cm$^3$ of water and 0.12 g (3 mmol) of sodium hydroxide. Reaction time: 1 h 15 min; ether extraction (4×7 cm$^3$). After treatment, 0.15 g of epoxide 2g were obtained (macrobore GC purity>97.5%), having a yield of 80%.

MW: 229.476; $^1$H NMR: 3.75 (d, 1H, J=4.2 Hz); 2.90–1.40 (m, 6H). IR in cm$^{-1}$ (film): 1410–1335–1240–1070 (broad)–910–860–840–790–770. Microanalysis: C$_6$H$_7$BrClFO; F. % C 32.07 H 3.47; Calc. % 31.40 3.07

EXAMPLE 24

Preparation of 1-methyl-2,2,6,6-tetrachlorocyclohexanol 1j 3.78 g (16 mmol) of 2,2,6,6-tetrachlorocyclohexanone were weighed into an oven-dried 50-cm$^3$ two-necked flask fitted with a thermometer and under argon atmosphere. 29 cm$^3$ of anhydrous THF (tetrahydrofuran) were introduced and the reaction mixture was cooled to −30° C. 14 cm$^3$ (16.8 mmol) of approximately 1.2M methylmagnesium iodide in ether were then added while the temperature was checked.

Magnetic stirring was continued for 15 min and then the temperature was returned to 0° C. over 45 min. 10 cm$^3$ of a 1N aqueous hydrochloric acid solution were then added at 0° C., and the material was extracted with ether, dried over MgSO$_4$, filtered and evaporated down. 3.97 g of an oil which crystallized on cooling were obtained, having a 98% crude yield of compound 1j. The alcohol 1j can be purified by flash chromatography on silica (eluent: ether/petroleum ether=90/10). m.p.=82° C. MW: 251.969; $^1$H NMR: 2.95–1.50 (m, 6H); 2.80 (s, 1H mobile); 1.92 (s, 3H). $^{13}$C NMR (acetone-d$_6$): 95.7 (C$_2$ and C$_6$); 80.6 (C$_3$ and C$_5$); 20.7 (C$_4$); 18.8 (C$_7$). IR in cm$^{-1}$: $v_{OH}$=3580 MS (m/e) EI: 258–256–254–252–250 (M+, 0.19–0.45–1.65–3.23–2.68); 203–201–199–197 (0.6–2.0–5.7–5.9); 175–173–171–169 (0.6–2.2–5.6–5.7); 130–128–126 (2.85–15.55–23.9); 107–105 (33.05–100.00); 92 (7.67); 77 (6.8); 65 (4.2); 45 (10.0); 43 (66.5); 41 (5.4). Microanalysis: C$_7$H$_{10}$Cl$_4$O; F. % C 33.37 H 4.00; Calc. % 33.49 4.08

EXAMPLE 25

Preparation of 1,3,3-trichloro-2-methyl-7-oxabicyclo[4.1.0]heptane 2h

The same procedure was employed as for the preparation of 2e in Example 17: it was performed with 3.97 g (15.75 mmol) of crude alcohol 1j, 20 cm$^3$ of distilled water and 2.4 g (60 mmol) of sodium hydroxide; reaction time was 1 h 15 min; ether extraction (5×40 cm$^3$); 3.29 g of epoxide 2h were obtained having a 95.5% yield based on the ketone (macrobore GC purity>99%)

b.p.=47° C./0.35 mm Hg; MW: 215.506; $^1$H NMR (CCl$_4$): 2.80–1.35 (m, 6H); 1.84 (s, 3H) IR in cm$^{-1}$ (film): 1445–1340–1080–980–945–860–760–715–665; $^{13}$C NMR (C$_6$D$_6$): 9.10 (C$_3$); 85.8 (C$_1$); 68.3 (C$_2$); 40.2 (C$_4$); 32.8 (C$_6$); 18.6 (C$_5$); 14.9 (C$_7$). Microanalysis: C$_7$H$_9$Cl$_3$O; F. % C 39.64 H 4.52; Calc. % 39.01 4.21.

EXAMPLE 26

Preparation of 1-vinyl-2,2,6.6-tetrachlorocyclohexanol 1k 2 g (8.28 mmol) of 2,2,6,6-tetrachlorocyclohexanone in solution in 8 cm$^3$ of anhydrous THF were added over 5 min at room temperature using a syringe-driver to 18.4 ml (16.9 mmol) of 0.9M vinylmagnesium bromide in THF under argon atmosphere (the temperature of the reaction mixture then rose to approximately 50° C.). Stirring was continued for 3 h at room temperature. 16 cm$^3$ of water were introduced and then 15 cm$^3$ of a 1N aqueous hydrochloric acid solution were added. The mixture was extracted with ether (3×50 cm$^3$), dried over MgSO$_4$, filtered and evaporated down. The crude product was purified by flash chromatography on silica (eluent: ether/petroleum ether=5/95). Three fractions were obtained: 0.05 g of pure epoxide 2i, 0.36 g of a mixture of epoxide 2i/alcohol 1k=39/61 (macrobore GC determination) and 1.18 g of pure alcohol 1k. The overall yield of epoxide 2i was therefore 11% and that of alcohol 1k 63%. Characteristics of the epoxide 2i: see Example 27. Characteristics of the alcohol 1k:

m.p.=79° C. MW: 263.98 $^1$H NMR: 6.95–6.55 (dd, 1H); 5.85–5.55 (m, 2H); 2.90 (s, 1H mobile); 2.95–1.30 (m, 6H). Microanalysis: C$_8$H$_{10}$Cl$_4$O; F. % C 36.80 H 3.69; Calc. % 36.40 3.82

EXAMPLE 27

Preparation of 1,3,3-trichloro-2-vinyl-7-oxabicyclo [4.1.0]heptane 2i

The same procedure was employed as for the preparation of 2e in Example 17: it was performed with 1.14 g (4.32 mmol) of pure alcohol 1k, 12 cm$^3$ of distilled water and 0.5 g (12.5 mmol) of sodium hydroxide; reaction time was 1 h 15 min; ether extraction (4×25 cm$^3$); the crude product was employed as such (crude yld=90.5%) or purified by flash chromatography on silica (eluent: ether/petroleum ether=3/97): 0.88 g of epoxide 2i were obtained, that was a 90% yield (macrobore GC purity>98.6%) MW: 227.519; $^1$H NMR: 6.75–6.30 (m, 1H); 5.80–5.45 (m, 2H); 3.00–1.25 (m, 6H). $^{13}$C NMR: 126.1 ($C_7$); 123.1 ($C_8$); 88.35 ($C_3$); 85.5 ($C_1$); 70.0 ($C_2$); 39.75 ($C_4$); 32.4 ($C_6$); 18.3 ($C_5$). IR in cm$^{-1}$ (film): 1080–940–875–785–735.

EXAMPLE 28

Preparation of 1-allyl-2,2,6,6-tetrachlorocyclohexanol 1l 0.95 g (4.03 mmol) of 2,2,6,6-tetrachlorocyclohexanone were weighed into an oven-dried 25-cm$^3$ two-necked flask fitted with a thermometer and under argon atmosphere. 6 cm$^3$ of anhydrous THF were added and the reaction mixture was cooled to –30° C. 13 cm$^3$ (4.8 mmol) of allylmagnesium bromide (0.37M) were then added while the temperature was controlled at –30° C., allowed to react for 30 min, and the mixture was hydrolyzed between –25° C. and –10° C. with a 5% ammonium chloride solution. It was extracted 5 times with ether, dried, filtered and evaporated down. 1.12 g of an oil which crystallized when cold were obtained; the crude yield of the alcohol 1l was 100%.

m.p.=50° C.; MW: 278.010; $^1$H NMR: 6.20–5.65 (m, 1H); 5.30–4.95 (m, 2H); 3.20–3.00 (d, 2H, J=6.5 Hz and s, 1H mobile); 2.90–1.35 (m, 6H). $^{13}$C NMR: 133.3 ($C_9$); 122.1 ($C_8$); 95.4 ($C_2$ and $C_6$); 79.5 ($C_1$); 42.2 ($C_3$ and $C_5$); 36.8 ($C_7$); 20.5 ($C_4$). IR in cm$^{-1}$ (film): $\nu_{OH}$=3520; $\nu_{C=C}$=1640–915.

EXAMPLE 29

Preparation of 2-allyl-1,3,3-trichloro-7-oxabicyclo [4.1.0]heptane 2j

The same procedure was employed as for the preparation of 2e in Example 17: it was performed with 1.12 g (4.03 mmol) of crude alcohol 1l, 5.5 cm$^3$ of distilled water and 0.6 g (12.5 mmol) of sodium hydroxide; reaction time was 1 h 15 min followed by ether extraction; the crude product was employed as such (crude yld=90.5%) or purified by flash chromatography on silica (eluent: ether/petroleum ether=3/97): 0.89 g of epoxide 2j were obtained, that was a 92% yield (macrobore GC purity>98.6%).

MW: 241.545; $^1$H NMR: 6.25–4.70 (m, 3H); 3.10 (d, 2H, J=7 Hz); 2.85–1.10 (m, 6H). $^{13}$C NMR: 132.5 ($C_8$); 118.0 ($C_9$); 90.6 ($C_3$); 85.0 ($C_1$); 68.4 ($C_2$); 40.0 ($C_7$); 32.5 ($C_4$ and $C_6$); 18.4 ($C_5$). IR in cm$^{-1}$ (film): 3080–1640–1430–1080–920–875–780–730. Microanalysis: $C_7H_9Cl_3O$; F. % C 45.01 H 4.32; Calc. % 44.75 4.59

EXAMPLE 30

Preparation of 2,2,6-trichloro-6-fluoro-1-methylcyclohexanol 1m 4 cm$^3$ of HF/pyridine complex (Aldrich 18,422-5) were introduced into a 20-cm$^3$ polyethylene flask fitted with magnetic stirring, a septum and an exit towards the exhaust hood. 1.92 g (8.91 mmol) of epoxide 2h were added over 20 min at –10° C., the mixture was left to react at this temperature for 1 h 10 min and the reaction mixture was then allowed to return to room temperature (10 min). It was hydrolyzed at –5° C. with 12 cm$^3$ of distilled water (5 min), was extracted with dichloromethane (4×20 cm$^3$), dried over $MgSO_4$, filtered and evaporated down. The crude product was purified by flash chromatography on silica (eluent: ether/petroleum ether=5/95): 1.79 g of a mixture of diastereoisomers of the alcohols were obtained, 1m/1m'=95/5 (macrobore GC determination). The overall reaction yield was 85.5%.

Characteristics of the predominant isomer 1m:

m.p.=95° C. (mixture 1m/1m'); MW: 235.515; $^1$H NMR: 2.90 (s, 1H mobile); 2.85–1.60 (m, 6H); 1.75 (s, 3H). $^{13}$C NMR (100 MHz): 115.2 (d, $C_2$, J=245 Hz); 95.39 (s, $C_6$); 80.01 (d, $C_1$, J=19 Hz); 42.31 (s, $C_5$); 36.64 (d, $C_3$, J=21 Hz); 19.79 (s, $C_7$); 19.39 (s, $C_4$). IR in cm$^{-1}$ (film): $\nu_{OH}$=3560. Microanalysis: $C_7H_{10}Cl_3FO$; F. % C 35.80 H 4.15; Calc. % 35.70 4.28.

EXAMPLE 31

Preparation of 3,3-dichloro-1-fluoro-2-methyl-7-oxabicyclo[4.1.0]heptane 2k

The same procedure was employed as for the production of 2e in Example 17: it was performed with 1.68 g (7.13 mmol) of alcohol 1m (containing 5% of stereoisomer 1m'), 12 cm$^3$ of distilled water and 1 g (25 mmol) of sodium hydroxide; reaction time 1 h 15 min; ether extraction (4×25 cm$^3$); 1.35 g of a crude mixture were obtained (macrobore GC overall purity>99.7%), of epoxides 2k, 2k', 2k" in respective proportions of 2k/2k'/2k"=89/4.5/6.5, having a crude yield of 95%.

Characteristics of the predominant isomer 2k

MW: 199.054; $^1$H NMR: 2.50–1.60 (m, 6H); 1.75 (s, 3H). IR in cm$^{-1}$ (film): 1260–1195–1160–1105 to 1075–930–885–880–770–730. Microanalysis: $C_7H_9Cl_2FO$; F. % C 42.38 H 4.49; Calc. 42.24 4.56

EXAMPLE 32

Preparation of 2,2-dichloro-6,6-difluoro-1-methylcyclohexanol 1n

The same procedure was employed as for the preparation of 1m in Example 30: it was performed with 1 g (5.02 mmol) of the mixture of epoxides 2k/2k'/2k"=89/4.5/6.5 added over 16 min at 0° C., allowed to react at this temperature for 20 min and the reaction mixture then allowed to return to room temperature (1 h 15 min). The crude product was purified by flash chromatography on silica (eluent: ether/petroleum ether=5/95): 0.94 g of a mixture of the alcohols 1n/1n'/1n"=89/4.5/6.5 (macrobore GC determination) was obtained. The overall reaction yield was 85.5%.

Characteristics of the predominant isomer 1n:

m.p.=58.59° C. (mixture 1n/1n'/1n"); MW: 219.060; $^1$H NMR: 2.50 (s, 1H mobile); 3.05–1.45 (m, 6H); 1.65 (s, broad, 3H). IR in cm$^{-1}$: $\nu_{OH}$=3590. Microanalysis: $C_7H_{10}Cl_2F_2O$; F. % C 39.14 H 4.78; Calc. % 38.38 4.60.

EXAMPLE 33

Preparation of 1-chloro-3,3-difluoro-2-methyl-7-oxabicyclo[4.1.0]heptane 2l

The same procedure was employed as for the preparation of 2e in Example 17: it was performed with 1.53 g (6.98 mmol) of the mixture of alcohols 1n/1n'/1n"=89/4.5/6.5, 10 cm³ of distilled water and 0.8 g (20 mmol) of sodium hydroxide; reaction time was 1 h 15 min; ether extraction (4×15 cm³); 1.19 g of a crude mixture were obtained (macrobore GC overall purity>99%), of epoxides 2l, 2l', 2l" which could not be separated by macrobore GC and, therefore, a proportion of 2l/2l'/2l"=89/4.5/6.5 was assumed having a crude yield (pure) of 93%.

MW: 182.599; $^1$H NMR: 2.79–1.42 (m, 6H); 1.65 (s, 3H). IR in cm$^{-1}$ (film): 1360–1330–1265–1200–1165–1100–1040–990–960–915–890–860. Microanalysis: $C_7H_9ClF_2O$; F. % C 45.74 H 5.17; Calc. % 46.05 4.97.

EXAMPLE 34

Preparation of 3-chlorophenol 4d 1.01 g (5.01 mmol) of epoxide 2a in solution in 3 cm³ of anhydrous DMF (dimethyl formamide) were heated to reflux for 3 h. The solution was acidified (pH=1) with 3N HCl, extracted with ether (4×20 cm³), dried over $MgSO_4$, filtered and evaporated down. The crude product obtained was purified by flash chromatography on silica (eluent: ether/petroleum ether=10/90). 0.55 g of phenol 4d were obtained, the yield of compound 4d was 83.5% (macrobore GC purity>95%).

m.p.=33°–35° C. b.p.=214° C. MW: 128.559; $^1$H NMR: 7.5–6.5 (m, 4H): 6.0 (s, broad, 1H mobile). IR in cm$^{-1}$: $v_{OH}$=3550 (broad): $v_{C=C}$=1590. Aldrich product: ref. C6,280–8.

Evidence for 2,3-dichloro-2-cyclohexen-1-one 8:

During the purification on silica, a fraction was isolated containing approximately 8 mg of a product (macrobore GC purity of 71%) whose analysis ($^1$H NMR, 80 MHz, IR and a GC/mass) suggests that it was 2,3-dichloro-2-cyclohexen-1-one 8.

MW: 165.020; $^1$H NMR: 2.95–2.45 (m, 4H); 2.35–1.85 (q, 2H). IR in cm$^{-1}$: $v_{C=O}$=1690; $v_{C=C}$=1590. MS (70 eV) m/e: 168–166–164 (M+; 5.2–31.6–51.6); 140–138–136 (10.6–62.7–100.0); 129 (13.6); 110 (15.5); 108 (22.2); 103–101 (5.9–19.1); 75 (13.4); 73 (35.5); 65 (26.9); 55 (39.6).

EXAMPLE 35

Preparation of 3-chloro-2-methylphenol 4e 2 g (9.28 mmol) of epoxide 2h in solution in 5 cm³ of anhydrous DMF were heated to reflux for 3 h. The solution was acidified (pH=1) with 3N HCl, extracted with ether (4×25 cm³), dried over $MgSO_4$, filtered and evaporated down. The crude product obtained was purified by flash chromatography on silica (eluent: ether/petroleum ether=5/95). 1.18 g of phenol 4e were obtained (macrobore GC purity>96%). The yield of compound 4e was 89%.

m.p.=84° C. MW: 142.586; $^1$H NMR ($CCl_4$): 7.10–6.75 (d, 2H); 6.75–6.40 (m, 1H); 4.90 (s, 1H mobile); 2.20 (s, 3H). $^{13}$C NMR ($CCl_4$): 154.2 ($C_1$): 135.2 ($C_3$); 126.7 ($C_5$); 122.7 ($C_2$); 121.6 ($C_4$); 113.3 ($C_6$); 12.3 ($C_7$). IR in cm$^{-1}$ ($CCl_4$): $v_{OH}$=3600; $v_{C=C}$=1585. Microanalysis: $C_7H_7ClO$; F. % C 58.37 H 5.06; Calc. % 58.96 4.94.

EXAMPLE 36

Preparation of 3-chloro-2-vinylphenol 4f 0.84 g (3.69 mmol) of epoxide 2i in solution in 4 cm³ of anhydrous DMF were heated to reflux for 3 h 30 min. The solution was acidified (pH=1) with 3N HCl, extracted with ether (4×20 cm³), dried over $MgSO_4$, filtered and evaporated down. The crude product obtained was purified by flash chromatography on silica (eluent: ether/petroleum ether=5/95). 0.43 g of phenol 4f were obtained (macrobore GC purity>99%). The yield of compound 4f was 75.5%.

m.p.=48° C.; MW: 154.597; $^1$H NMR: 7.25–6.55 (m, 4H); 5.85–5.55 (m, 3H of which 1H mobile). IR in cm$^{-1}$: $v_{OH}$=3260; $v_{C=C}$=1630, 1595, 1585. Microanalysis: $C_8H_7ClO$; F. % C 62.15 H 4.56; Calc. % 62.30 4.48.

EXAMPLE 37

Preparation of 2-allyl-3-chlorophenol 4g 2 g (8.28 mmol) of epoxide 2j in solution in 5 cm³ of anhydrous DMF were heated to reflux for 5 h. The solution was acidified (pH<1) with 3N HCl, extracted with ether and concentrated, and a 3N sodium hydroxide solution was added to the ether phase (while the mixture was kept stirred for 5 to 10 min), the ether phase was removed and the material washed once with ether. The aqueous phase was acidified using a solution with 3N HCl (pH=1) and extracted with ether (4×30 cm³), dried over $MgSO_4$, filtered and evaporated down. 1.24 g of phenol 4g were obtained as a liquid whose macrobore GC purity was higher than 97%. The yield of phenol 4g was 89%.

MW: 168.624; $^1$H NMR: 7.05–6.50 (m, 3H); 6.20–5.65 (m, 1H); 5.60–4.85 (s, 1H mobile) 3.55 (d, 2H, J=6.1 Hz). $^{13}$C NMR: 154, 85 ($C_1$); 134.9 ($C_3$); 134.5 ($C_8$); 127.6 ($C_5$); 123.95 ($C_2$); 121.8 ($C_4$); 115.85 ($C_9$); 114.1 ($C_6$); 31.2 ($C_7$). IR in cm$^{-1}$ (film): $v_{OH}$=3500; $v_{C=C}$=3080–1640–1580–910. MS (m/e) EI: 170–168 (M+, 32.2–100.0); 155–153 (17.8–59.0); 143–141 (6.6–22.9); 133 (43.2); 132 (9.4); 127–125 (10.8–34.1); 115 (24.9); 105 (37.7); 103 (18.7); 79 (11.7); 78 (11.9); 77 (43.8); 63 (10.5); 51 (33.3); 49 (10.4). Microanalysis: $C_9H_9ClO$; F. % C 63.80 H 5.26; Calc. % 64.11 5.38.

EXAMPLE 38

Preparation of 3-fluoro-2-methylphenol 4h 0.65 g (3.69 mmol) of epoxide 2l (a mixture of 2l, 2l', 2l" above) in solution in 3 cm³ of anhydrous DMF were heated to reflux for 3 h; 91% of transposition ketone 6b was then detected by macrobore GC (verification by mass/GC coupling). 0.86 g (2 eq.) of DMAP were then added and the mixture was again heated to reflux for 3 h. It was acidified (pH=1) with 3N HCl, extracted with ether, concentrated, and a 3N sodium hydroxide solution was added to the ether phase (while the mixture was kept stirred for 5 to 10 min), the ether phase was removed and the material was washed once with ether. The aqueous phase was acidified using a solution with 3N HCl (pH=1) and was extracted with ether (4×15 cm³), dried over $MgSO_4$, filtered and evaporated down. The crude product obtained was purified by flash chromatography on silica (eluent: ether/petroleum ether=5/95). 0.10 g of phenol 4h were obtained (macrobore GC purity>97%). The yield of compound 4h was 22%.

MW: 126.132; $^1$H NMR: 7.15–6.30 (m, 3H); 5.15 (s, 1H mobile); 2.14 (d, 3H, J=2 Hz). IR in cm$^{-1}$: $v_{OH}$=345c (broad); $v_{C=C}$=1620 (weak), 1595. MS (m/e): 126 (M$^+$, 100); 125 (87); 109 (10.5); 108 (28); 107 (14.5); 97 (30.5); 95 (10); 77 (16.5); 49 (21).

EXAMPLE 39

Preparation of 3-fluorophenol 4i 0.90 g (4.86 mmol) of epoxide 2e in solution in 3 cm³ of anhydrous DMF were heated to reflux for 3 h. The solution was acidified (pH=1) with 3N HCl, extracted with ether (4×20 cm³) dried over MgSO₄ filtered and evaporated down. The crude product obtained was purified by flash chromatography on silica (eluent: ether/petroleum ether=10/90). 0.53 g of a mixture of the phenols 4i and 4d were obtained in a proportion of 4i/4d=76/24. The overall crude yield was 85%. The phenols 4i and 4d were identified by comparison with the commercial Aldrich products (using macrobore GC).

b.p.=178° C.; MW: 112.105; $^1$H NMR: 7.40–6.40 (m, 4H); 5.70 (s, broad, 1H mobile). IR in cm$^{-1}$ (film): $v_{OH}$=3350; $v_{C=C}$=1600; Reference: Aldrich F1,300-2.

EXAMPLE 40

Evidence for 2-allyl-2,3,3-trichlorocyclohexanone 6a 1.60 g (6.62 mmol) of epoxide 2j and 2 cm³ (25 mmol) of pyridine were heated to reflux for 24 h. After cooling, the mixture was acidified to pH=1 with 3N HCl, extracted with ether (3×30 cm³), dried over MgSO₄ filtered and evaporated down. The crude product was purified by flash chromatography on silica (eluent: ether/petroleum ether=1/99). The following were isolated (in the order of elution): starting epoxide 2j, 0.40 g of transposition ketone 6a (Yld=40%), traces of 2-allyl-2,3-dichloro-3-cyclohexenone 7 (evidence based on GC/mass) and phenol 4f.

Characteristics of 2-allyl-2,3,3-trichlorocyclohexanone 6a:

m.p.=42°–43° C.; W: 241.546; $^1$H NMR: 6.1–5.5 (m, 1H); 5.3–4.9 (m, 2H); 3.8–1.7 (m, 6H); 2.97 (d, 2H, J=7.3 Hz). $^{13}$C NMR (100 MHz): 198.93 (C₁); 132.38 (C₉); 118.98 (C₈); 95.30 (C₃); 76.89 (C₂); 41.40 (C₄); 37.99 (C₇ or C₆); 34.78 (C₆ or C₇); 21.07 (C₅). IR in cm$^{-1}$ (film): $v_{C=O}$=1740; $v_{C=C}$=3080–1645–920. MS (m/e) EI: 244–242–240 (M⁺, 0.68–1.36–1.31); 209–207–205 (5.8–26.7–45.0); 171–169 (33.5–100.0); 166–164–162 (8.1–40.3–67.1); 149 (14.2); 147 (17.0); 141 (15.1); 135 (24.1); 133 (14.6); 129–127 (28.1–81.3); 115 (16.7); 113 (39.7); 107 (10.8); 105 (41.05); 99 (10.0); 91 (52.1); 79 (52.6); 78 (16.0); 77 (75.0); 75 (15.1); 65 (23.1); 63 (14.0); 55 (82.9); 53 (17.4); 52 (14.5); 51 (41.7); 49 (11.0). Microanalysis: C₉H₁₁Cl₃O; F. % C 44.47 H 4.89; Calc. 44.75 4.59

Characteristics of 2-allyl-2,3-dichloro-3-cyclohexene-1-one 7:

MW: 205.085; $^1$H NMR: 6.1–5.4 (m, 1H); 5.2–4.8 (m, 2H); 4.3 (t, 1H, J=5.2 Hz); 3.2 (d, 1H, J=6.5 Hz); 3.1–1.6 (m, 6H). MS (m/e): 208–206–204 (M⁺, 1.3–7.5–10.8); 171–169 (32.0–100.0); 153–151 (8.7–17.0); 144–142 (13.3–39.7); 133 (36.0); 127 (16.1); 114 (12.2); 107 (34.1); 105 (23.1); 79 (81.8); 77 (37.9).

EXAMPLE 41

Preparation of 2-allyl-3-chlorophenol 4g from the ketone 6a 0.13 g (0.54 mmol) of ketone 6a in solution in 1 cm³ of anhydrous DMF were heated to reflux for 10 h. After cooling, the solution was acidified with 3N HCl and extracted with ether. A check was then made using macrobore GC that the predominant product (GC yield>90%) was indeed identical with the phenol 4g prepared above.

EXAMPLE 42

Preparation of 2,2,6-trichloro-6-fluorocyclohexanone 3a'

0.45 g (1.81 mmol) of hydrate 3a ($^{19}$F NMR determination: hydrate 3a/ketone 3a'=90.4/9.6) in solution in 10 cm³ of anhydrous benzene were introduced into a Dean-Stark vessel fitted with magnetic stirring and under argon atmosphere. The solution was heated to reflux overnight (at the end of reaction the appearance of a carbonyl band at about 1765 cm$^{-1}$ was observed by IR measurement carried out in benzene) and, after cooling the reaction mixture, the benzene was evaporated off. 0.28 g of ketone 3a' were obtained ($^{19}$F NMR determination: hydrate 3a/ketone 3a'=98.5/1.5).

The reaction yield was 70% of compound 3a'.

m.p.°C.=34; MW: 219.47; $^1$H NMR 200 MHz: 2.95–2.75 (m, 1H): 2.75–2.35 (m, 3H); 2.3–1.9 (m, 2H). $^{19}$F NMR (CDCl₃) 190 MHz: –104.00 (t, 0.94F, J=10.1 Hz); –105.7 (t, 0.06F, J=10.1 Hz), (D, C₁, J=22.5 Hz); $^{13}$C NMR (CDCl₃) 50 MHz: 185.02. 104.97 (d, C₆, J=257.8 Hz); 84.13 (C₂); 46.46 (C₃); 41.10 (d, C₅, J=21.2 Hz); 18.32 (d, C₄, J=7 Hz). IR in cm$^{-1}$ (C₆H₆): $v_{C=O}$: 1765. MS (m/e): 224–222–220–218 (M⁺, 0.29–2.04–6.28–6.65); 194–192–190 (1.20–3.94–3.95); 156–154–152 (2–10.3–14.83); 146 (6.4): 144 (5.7); 121–119 (32.0–100.0); 111 (9.2); 109 (14.9); 93 (22.9); 83 (16.7); 77 (13.5); 75 (43.7); 58 (13.5); 56 (24.8); 53 (10.1). Scanning as far as m/e=50.

The foregoing description of preferred embodiments of the invention have been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto and their equivalents.

What is claimed is:

1. A process for the synthesis of a halogenated or pseudohalogenated aromatic compound which comprises aromatization of a compound corresponding to the general formula (II):

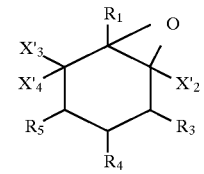

by the dehydrohalogenation of the compound of formula (II)
in which X'₂, X'₃ and X'₄ are the same or different and denote a halogen or a pseudohalogen;
in which R₁ denotes a hydrocarbon chain, or R₁ denotes hydrogen, or an aromatic group, aromatic ether, cycloalkyl ether, alkoxy, carboxyl, acyloxy, hydroxyl, cyano, amido, or imido;
in which R₄ denotes a hydrocarbon chain, or R₄ denotes hydrogen, or an aromatic group, carboxyl, fluorine atom, or carboxamide, or a radical joined to the hexane ring of formula II by a chalcogen or an element of Group V, wherein said radical is an amido, alkoxy or acyloxy;
in which the radicals R₃ and R₅ may be the same or different and denote a fluorine or hydrogen or hydrocarbon chain;
with the condition that, when R₁ is hydroxyl, cyano, amido, imido, ethoxy, benzyloxy, cyclohexyloxy and tertbutoxy, all the halogens cannot simultaneously be chlorine, and $R_3$, $R_4$ and $R_5$ simultaneously are hydrogen.

2. The process of claim 1 where said aromatization comprises converting the compound of formula (II) to a 1,1-diol and contacting said diol with a base in the presence of a dehydrating agent to produce a substituted phenol.

3. The process of claim 2 where said base is an organic amine or amide.

4. The process of claim 2 where said base is pyridine.

5. The process of claim 4 where said pyridine is used in combination with a 4 Å molecular sieve dehydrating agent.

6. The process of claim 1 wherein the compound of formula (II) is converted to a halohydrin with a Lewis Acid or Bronsted Acid and said halohydrin is converted to a phenol in the presence of a base.

7. The aromatization process of claim 1 where the compound of formula (II) is reacted in a base to produce a phenol.

8. The process of claim 7 where said compound is refluxed in the presence of an amine or amide to produce a phenol.

9. The process of claim 8 where said compound is refluxed in DMF and acidified to produce a phenol.

10. A process for the synthesis of a halogenated or pseudohalogenated aromatic compound according to claim 1 which comprises conversion of a compound of formula (II):

(a) to a diol and converting the diol to an aromatic compound; or (b) to a halohydrin and converting the halohydrin to an aromatic compound; or (c) to an aromatic compound by reaction with a base; or (d) to a ketone compound directly, and converting said ketone compound to an aromatic compound.

11. A process for the synthesis of a halogenated or pseudohalogenated aromatic compound according to claim 10 which comprises conversion of a compound of formula (II) to a ketone, followed by converting said ketone to an intermediate, wherein said intermediate is a thioketone, acetal, imine, oxime, compound having double bonds obtained by reaction of a compound having acidic methylenes on ketones, and converting said intermediate to an aromatic compound.

* * * * *